United States Patent
Collier et al.

(10) Patent No.: US 7,977,361 B2
(45) Date of Patent: *Jul. 12, 2011

(54) NITRO-IMIDAZOLE HYPOXIA IMAGING AGENT

(75) Inventors: Thomas Lee Collier, Perkasie, PA (US);
Brian A. Duclos, Kalamazoo, MI (US);
Umesh B. Gangadharmath, Los Angeles, CA (US); Zhiyong Gao, Wynnewood, PA (US); Farhad Karimi, Mansfield, MA (US); Dhanalakshmi Kasi, Los Angeles, CA (US); Hartmuth C. Kolb, Playa Del Rey, CA (US); Qianwa Liang, Hacienda Heights, CA (US); Henry Clifton Padgett, Hermosa Beach, CA (US); Joseph C. Walsh, Pacific Palisades, CA (US); Tieming Zhao, Los Angeles, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/836,926

(22) Filed: Jul. 15, 2010

(65) Prior Publication Data

US 2011/0002850 A1 Jan. 6, 2011

Related U.S. Application Data

(62) Division of application No. 12/098,390, filed on Apr. 4, 2008, now Pat. No. 7,807,394.

(60) Provisional application No. 60/921,932, filed on Apr. 5, 2007, provisional application No. 60/964,254, filed on Aug. 10, 2007.

(51) Int. Cl.
*C07D 249/04* (2006.01)
*A61K 31/4192* (2006.01)

(52) U.S. Cl. ........................ 514/359; 514/397; 548/255

(58) Field of Classification Search ........................ None
See application file for complete search history.

(56) References Cited

U.S. PATENT DOCUMENTS

| | | | |
|---|---|---|---|
| 5,674,693 A | | 10/1997 | Raleigh et al. |
| 5,721,265 A | * | 2/1998 | Tracy et al. ............ 514/396 |
| 7,807,394 B2 | * | 10/2010 | Kolb et al. ............ 435/7.23 |

FOREIGN PATENT DOCUMENTS

| | | |
|---|---|---|
| WO | 9604249 A1 | 2/1996 |
| WO | 0112575 A1 | 2/2001 |

OTHER PUBLICATIONS

Houghten, et al., Peptides: The Wave of the Future, 2nd International Peptide Symposium in Conjunction with the 17th American Symposium, Jun. 9-14, 2001, San Diego, California.

Adams, G.E. "Hypoxia-mediated Drugs for Radiation and Chemotherapy", Cancer (1981), 48:696-707.
Bentzen, et al., "Feasibility of Detecting Hypoxia in Experimental Mouse Tumours with 18[F]-fluorinated Tracers and Positron Emission Tomography", Acta. Oncol. (2000), 39:629-637.
Brizel, et al., "Tumour Oxygenation Predicts for the Likelihood of Distant Metastases in Human Soft Tissue Sarcoma", Cancer Res., (1996), 56:941-943.
Chao, et al., "A Novel Approach to Overcome Hypoxic Tumor Resistance: Cu-ATSM-Guided Intensity-Modulated Radiation Therapy", Int. J. Radiat. Oncol. Biol. Phys. (2001), 49:1171-1182.
Fujibayashi, et al., "Copper-62-ATSM: A New Hypoxia Imaging Agent with High Membrane Permeability and Low Redox Potential", J. Nucl. Med. (1997), 38:1155-1160.
Gronroos, et al., "Pharmacokinetics of [18F]FETNIM: A Potential Hypoxia Marker for PET", J. Nucl. Med. (2001), 42:1397-1404.
Hockel, et al., "Association between Tumor Hypoxia and Malignant Progression in Advanced Cancer of the Uterine Cervix", Cancer Res. (1996), 45:4509-4515.
Huisgen, R., "1,3-Dipoloar Clycloadditions—Introduction, Survey, Mechanism", (Padwa, A., ed.), pp. 1-176, Wiley, 1984.
Evans, et al., "Noninvasive Detection of Tumor Hypoxia Using the 2-Nitroimidazole [18]EF-1", J. Nucl. Med. (1999), 41(2):327-336.
Ishikawa, et al., "Development of [18F]FRP-170 Injection for Imaging Hypoxia by PET", Kaku Igaku, (2005), 42:1-10, [Article in Japanese, English Abstract obtained].
Jorgensen, K., "Catalytic Asymmetric Hetero-Diels—Alder Reactions of Carbonyl Compounds and Imines", Angew. Chem. Int. Ed. Engl. (2000), 39:3558-3588.
Kolb, et al., "Click Chemistry: Diverse Chemical Function from a Few Good Reactions", Angew. Chem. Int. Ed. (2001), 40:2004-2021.
Kolb, et al., "The Growing Impact of Click Chemistry on Drug Discovery", Drug Discovery Today (2003), 8:1128-1137.
Krasinski, et al., "Direct Synthesis of 1,5-Disubstituted-4-magnesio-1,2,3-triazoles, Revisited", Organic Letters (2004), 6:1237-1240.
Lee, et al., "A Potent and Highly Selective Inhibitor of Human alpha-1,3-Fucosyltransferase via Click Chemistry", J. Chem. Soc. (2003), 125:9588-9589.

(Continued)

*Primary Examiner* — Yong Chu
*Assistant Examiner* — Michael Barker
(74) *Attorney, Agent, or Firm* — Joshua B. Ryan

(57) ABSTRACT

The present invention relates to novel radioactively labeled bioreducible tracers of Formula I useful for detecting hypoxic tumors or ischemic tissue in vivo. In one embodiment, the tracers consist of a 2-nitroimidazole moiety, a triazole, metabolically stable linker with pharmacokinetics enhancing substituents, and a radioisotope. The preferred in vivo imaging modality is positron emission tomography.

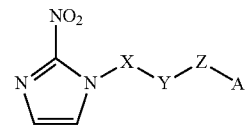

31 Claims, 6 Drawing Sheets

OTHER PUBLICATIONS

Lewis, et al., Click Chemistry in Situ: Acetylcholinesterase as a Reaction Vessel for the Selective Assembly of a Femtomolar Inhibitor from an Array of Building Blocks, Angew. Chem. Int. Ed. (2002), 41:1053-1057.

Manetsch, et al., "In Situ Click Chemistry: Enzyme Inhibitors Made to Their Own Specifications", J. Am. Chem. Soc. (2004), 126:12809-12818.

Mocharla, et al., "In Situ Click Chemistry: Enzyme-Generated Inhibitors of Carbonic Anhydrase II", Angew. Chem, Int. Ed. (2005), 44:116-120.

Moulder, et al., "Hypoxic Fractions of Solid Tumors: Experimental Techniques, Methods of Analysis, and a Survey of Existing Data", Int. J. Radiation Oncology Biol. Phys. (1984), 10:695-712.

Nordsmark, et al., "Pretreatment Oxygenation Predicts Radiation in Response in Advanced Squamous Cell Carcinoma of the Head and Neck", Radiother. Oncol. (1996), 41:31-39.

Rasey, et al., "Determing Hypoxic Fraction in a Rat Glioma by Uptake of Radiolabeled Fluromisonidazole", Radiat. Res. (2000), 153:84-92.

Rosotovtsev, et al., "A Stepwise Cycloaddition Process: Copper(I)-Catalyzed Regioselective "Ligation" of Azides and Terminal Alkynes", Angew. Chem. Int. Ed. (2002), 41:2596-2599.

Seddon, et al., "The Role of Functional and Molecular Imaging in Cancer Drug Discovery and Development", Brit. J. Radiol. (2003), 76:S128-S138.

Tietze, et al., "Hetero Diels-Alder Reactions in Organic Chemistry", Top. Curr. Chem. (1997), 189:1-120.

Tornoe, et al., "Peptidotriazoles on Solid Phase: [1,2,3]-Triazoles by Regiospecific Copper(I)-Catalyzed 1,3-Dipolar Cycoladditions of Terminal Alkynes to Azides", J. Org. Chem. (2002), 67:3057-3064.

Vaupel, et al., "Oxygenation of Human Tumors: Evaluation of Tissue Oxygen Distribution in Breast Cancers by Computerized O2 Tension Measurements", Cancer Res. (1991), 51:3316-3322.

Wang, et al., "Biconjugation by Copper(I)-Catalyzed Azide-Alkyne [3+2] Cycloaddition", J. Am. Chem. Soc. (2003), 125:3192-3193.

Wang, et al., "Positron Emission Tomography: Application in Drug Discovery and Drug Development", Curr. Top. Med. Chem. (2005), 5:1053-1075.

Whiting, et al., "Inhibitors of HIV-1 Protease by Using in Situ Click Chemistry", Angew. Chem. (2006), 118:1463-1467.

Yang, et al., "Development of F-18-labeled Fluoroerythronitroimidazole as a PET Agent for Imaging Tumor Hypoxia" Radiology (1995), 194:795-800.

* cited by examiner

Figure 1:
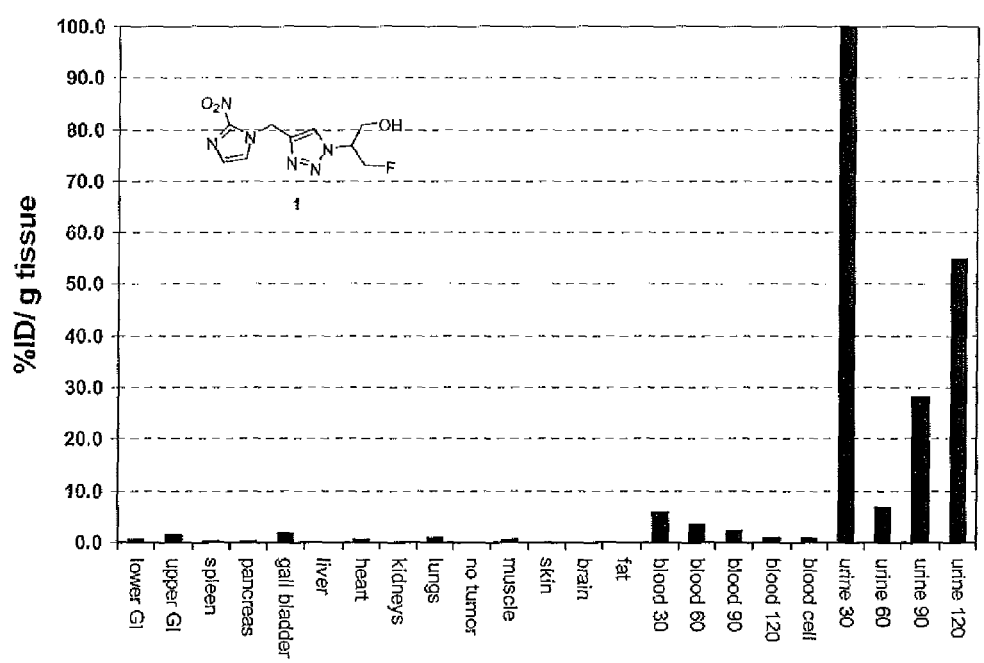

Figure 1: Bio-distribution of Compound 1 in male white mouse 120 min post IV injection (200 µl of a 5 mM solution).

Figure 2:
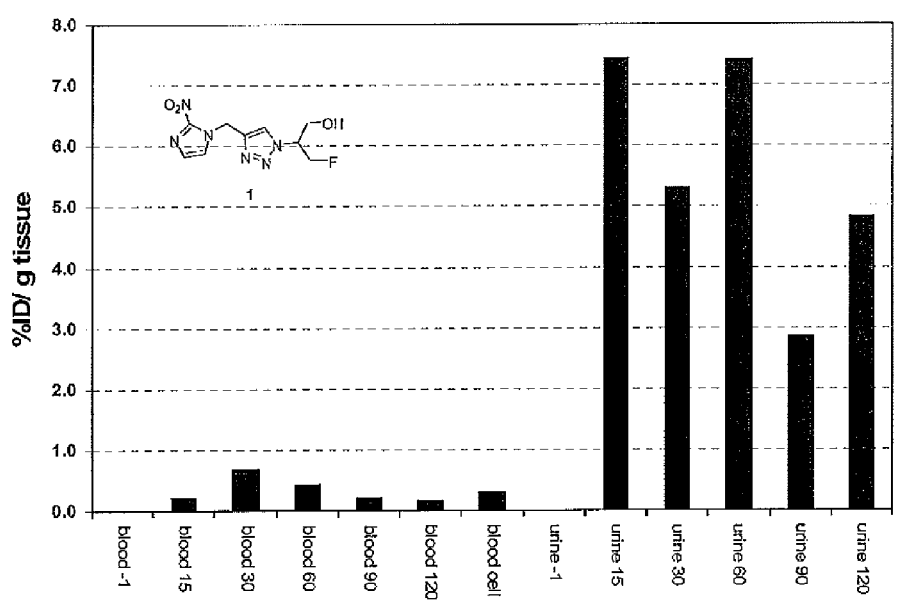

Figure 2: Plasma and Urine Pharmacology Study of Compound 1 in Wild-type Rat (1 ml at 10 mM concentration).

Figure 6: PET Images
Hypoxic NCI xenograft tumor in an athymic mouse.
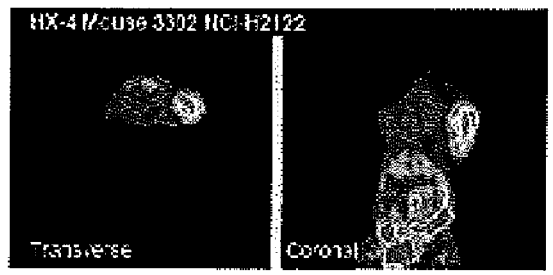
Hypoxic LS174T xenograft tumor in an athymic mouse.
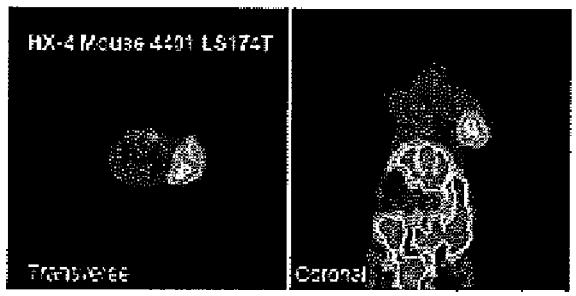
Hypoxic A427 xenograft tumor in an athymic mouse.
Non-hypoxic BXPC3 xenograft tumor in an athymic rat:

US 7,977,361 B2

NITRO-IMIDAZOLE HYPOXIA IMAGING AGENT

CROSS-REFERENCE TO RELATED APPLICATIONS

This application is a divisional application of U.S. application Ser. No. 12/098,390, filed on Apr. 4, 2008. U.S. application Ser. No. 12/098,390 is incorporated herein by reference. The present application and U.S. application Ser. No. 12/098,390 claim priority to U.S. (provisional) Application Ser. Nos. 60/964,254 and 60/921,932, filed on Aug. 10, 2007 and Apr. 5, 2007, respectively. These provisional patent applications are incorporated by reference herein.

FIELD OF THE INVENTION

The present invention relates to novel radioactively labeled bioreducible tracers useful for detecting hypoxic cells in vivo. In one aspect, the present application relates to a novel hypoxia imaging agent that displays low background uptake leading to good tumor to background ratios.

BACKGROUND OF THE INVENTION

Positron Emission Tomography (PET) is a molecular imaging technology that is used effectively for the detection of disease. PET imaging systems create images based on the distribution of positron-emitting isotopes in the tissue of a patient. The isotopes are typically administered to a patient by injection of probe molecules that comprise a positron-emitting isotope, such as F-18, C-11, N-13 or O-15, covalently attached to a molecule that is readily metabolized or localized in cells (e.g., glucose) or that chemically binds to receptor sites within cells. In some cases, the isotope is administered to the patient as an ionic solution or by inhalation. One of the most widely used positron-emitter labeled PET molecular imaging probes is 2-deoxy-2-[$^{18}$F]fluoro-D-glucose ([$^{18}$F]FDG).

PET scanning using the glucose analog [$^{18}$F]FDG, which primarily targets glucose transporters and hexokinase, is an accurate clinical tool for the early detection, staging, and restaging of cancer. PET-FDG imaging is also used to monitor cancer chemotherapy and chemoradiotherapy because early changes in glucose utilization have been shown to correlate with outcome predictions. A characteristic feature of tumor cells is their accelerated glycolysis rate, which results from the high metabolic demands of rapidly proliferating tumor tissue. Like glucose, FDG is taken up by cancer cells via glucose transporters and is phosphorylated by hexokinase to FDG-6 phosphate. FDG-6 phosphate cannot proceed any further in the glycolysis chain, or leave the cell due to its charge, allowing cells with high glycolysis rates to be detected.

Although useful in many contexts, limitations of FDG-PET imaging for monitoring cancer exist as well. Accumulation in inflammatory tissue limits the specificity of FDG-PET. Conversely, nonspecific FDG uptake may also limit the sensitivity of PET for tumor response prediction. Therapy induced cellular stress reactions have been shown to cause a temporary increase in FDG-uptake in tumor cell lines treated by radiotherapy and chemotherapeutic drugs. Further, physiologically high normal background activity (e.g. in the brain) can render the quantification of cancer-related FDG-uptake impossible in some areas of the body.

Due to these limitations, other PET imaging tracers are being developed to target other enzyme-mediated transformations in cancer tissue, such as 3'-[F-18]Fluoro-3'-deoxythymidine (FLT) for DNA replication, and [C-11](methyl) choline for choline kinase, as well as ultra high-specific activity receptor-ligand binding (e.g., 16α, [F-18]fluoroestradiol) and potentially gene expression (e.g., [F-18]fluoro-ganciclovir). Molecularly targeted agents have demonstrated great potential value for non-invasive PET imaging in cancers.

These studies have demonstrated the great value of non-invasive PET imaging for specific metabolic targets of cancer. Despite the clear clinical value of incorporating PET imaging into patient management, limitations do exist. In certain instances, current imaging probes lack specificity or have inadequate signal to background characteristics. In addition, new biological targets that are being tested for therapeutic intervention will require new imaging probes to evaluate therapeutic potential.

Thus, additional biomarkers are needed that show a very high affinity to, and specificity for, tumor targets to support cancer drug development and to provide health care providers with a means to accurately diagnose diseases and monitor treatment. Such imaging probes could dramatically improve the patient's outcome, allowing smaller tumors to be detected, with only nanomole quantities of the tracer injected into patients.

Key to the clinical success of cancer treatment is the ability to predict how a particular type of cancer will respond to treatment. In the specific case of tumors, factors such as the tumor's phenotype, size and location all dramatically affect therapeutic treatment decisions. While standard chemotherapeutic or radiation regimens are employed to treat a variety of tumors, certain tumor types resist standard therapeutic regimens and thus may worsen a patient's clinical outcome.

Due to the unique nature of cancer cell growth, its proliferative nature can offer clues for its therapeutic treatment. For instance, because of the rapid and disorganized growth of cancerous tumors, they oftentimes develop disorganized neovascularization leading to poorly vascularized environments. (Wang, J. and L. Maurer, *Positron Emission Tomography: Applications in Drug Discovery and Drug Development* Curr. Top. Med. Chem., 2005, 5: p. 1053-1075). In turn, environments that are removed 100-200 µm from blood supplies can become hypoxic, characterized by a tissue $pO_2$ of less than 10 mmHg. In response to these hypoxic conditions, tumor overexpression of hypoxia inducible factor-1 (HIF-1) leads to the up-regulation of several proteins necessary for tumor survival including vascular endothelial growth factor (VEGF), carbonic anhydrase-IX (CA-IX), and glycolysis enzymes.

Hypoxic tumors are clinically problematic: they resist both the effects of radiation and cytotoxic therapy which can result in treatment failure. (Adams, G., *Hypoxia-mediated drugs for radiation and chemotherapy*. Cancer, 1981. 48: p. 696-707; Moulder, J. and S. Rockwell, *Hypoxic fractions of solid tumors: experimental techniques, methods of analysis, and a survey of existing data*. Int. J. Radiat. Oncol. Biol. Phys., 1984, 10: p. 695-712; Nordsmark, M., M. Overgaard, and J. Overgaard, *Pretreatment oxygenation predicts radiation response in advanced squamous cell carcinoma of the head and neck*. Radiother. Oncol, 1996. 41: p. 31-39.) Moreover, hypoxic cancer cells have been linked to malignant cancers that are known to spread invasively throughout the patient. (Brizel, D. M., et al., *Tumour oxygenation predicts for the likelihood of distant metastases in human soft tissue sarcoma*. Cancer Res., 1996. 56: p. 941-943; Höckel, M., et al., *Association between tumor hypoxia and malignant progression in advanced cancer of the cervix*. Cancer Res., 1996. 56: p. 941-943.) Several types of human cancers are well known to become hypoxic including breast, cervical cancer and non-small cell lung cancer. (Vaupel, P., et al., *Oxygenation of human tumours: evaluation of tissue oxygen distribution in breast cancers by computerized $O_2$ tension measurements.* Cancer Res., 1991, 51: p. 3316-3322.)

Because hypoxic tumors respond poorly to both traditional radiation and cytotoxic therapies, several alternate approaches exist for treating hypoxic cancer cells including hyperbaric $O_2$, ARCON, radiosensitizers and bioreductive cytotoxic agents. (Seddon, B. M. and P. Workman, *The role of functional and molecular imaging in cancer drug discovery and development* Brit, J. Radial., 2003. 76: p. S 1 28-S 138.) In the last example, the bioreductive agents containing the nitroimidazole chemotype are reduced intracellularly, forming radical anion metabolites that eventually become trapped intracellularly. In oxic environments, the radical anion reacts with $O_2$ and returns to its premetabolized state.

Confirmation of tumor hypoxia in patients is necessary in order to appropriately plan bioreductive-based therapies for treatment. Determining tumor hypoxia via electrode measurements of $pO_2$ concentrations within the tumor is an impractical endeavor at best. In addition, it is only possible to interrogate superficial tumors with this technique. A more general and less invasive method for detecting the hypoxic nature of cancer cells relies on radioactively labeled, bioreducible tracers that localize within hypoxic cells inversely proportional to their cellular $pO_2$.

There are several bioreducible imaging agents that can detect hypoxic cells in vivo including [$^{18}$F]F-MISO (Rasey, J. S., et al., *Determining the hypoxic fraction in a rat glioma by uptake of radiolabeled fluoromisonidazole.* Radiat. Res., 2000. 153: p. 84-92; Bentzen, L., et al., *Feasibility of detecting hypoxia in experimental mouse tumours with $^{18}$F-fluorinated tracers and positron emission tomography: a study evaluating $^{18}$F-Fluoromisonidazole and [$^{18}$F]Fluoro-2-deoxy-D-glucose.* Acta. Oncol., 2000. 39: p. 629-637), [$^{18}$F] F-EF1 (Hustinx, R., et al., *Non-invasive assessment of tumor hypoxia with the 2-nitroimidazole $^{18}$F-EFI and PET* J. Nucl. Med., 1999. 4: p. 99P (abstract 401)), [$^{18}$F]-FETNIM (Chao, K. S., et al., *A novel approach to overcome hypoxic tumor resistance: Cu-ATSM-guided intensity-modulated radiation therapy.* Int. J. Radiat. Oncol. Biol. Phys., 2001. 49: p. 1171-1182; Yang, D. J., et al., *Development of $^{18}$F-labeled fluoroerythronitroimidazole as a PET agent for imaging tumor hypoxia.* Radiology, 1995. 194: p. 795-800; Gronroos, T., et al., *Pharmacokinetics of [$^{18}$F]-FETNIM. A potential hypoxia marker for PET* J. Nucl. Med., 2001. 42: p. 1397-1404), [$^{18}$F]FRP-170 (Ishikawa, Y., et al., *Development of [$^{18}$F] FRP-170 injection for imaging hypoxia by PET.*, Kaku Igaku., 2005, 42: p. 1-10.), and [$^{62}$Cu]-ATSM (Fujibayashi, Y., et al., *Copper-62-ATSM—a new hypoxia imaging agent with high membrane permeability and low redox potential.* J. Nucl. Med., 1997. 38: p. 1155-1160).

One of most clinically studied hypoxia markers is [$^{18}$F]-MISO, the fluorine analog of the hypoxic cell radiosensitizer misonidazole. [$^{18}$F]F-MISO successfully identifies hypoxic tumors in patients, however, its slow diffusion into hypoxic tumors requires longer uptake times before imaging and, in addition, high background uptake leads to small tumor to background ratios. As an alternative, several groups have prepared nitroimidazoles with less lipophilic character in an attempt to increase the tumor to background ratio by increasing the tracer's washout from normoxic tissue.

While these hypoxic imaging agents show clinical promise, there exists an unmet need for hypoxia tracers that possess enhanced pharmacokinetic profiles leading to peak signal to noise ratios in shorter periods for faster and potentially more accurate hypoxia assessments.

SUMMARY OF THE INVENTION

The present invention relates to novel hypoxia imaging agents that display low background uptake leading to high tumor to background ratios. More specifically, the present invention relates to novel 2-nitroimidazole based hypoxia imaging agents that display rapid, predominantly renal clearance, leading to low background uptake, low abdominal uptake and generally high tumor to background ratios.

The present invention relates to novel radioactively labeled bioreducible tracers useful for detecting hypoxic tumors in vivo. In one embodiment, the tracers consist of a 2-nitroimidazole moiety, a triazole, metabolically stable linker with pharmacokinetics enhancing substituents, and a radioisotope suitable for single photon emission computed tomography (SPECT) or positron emission tomography (PET) imaging. The preferred in vivo imaging modality is positron emission tomography. Because hypoxic cells resist cytotoxic and radiation therapies, and also possess an increased propensity of proliferation and propagation into nearby tissues, accurate assessment of the hypoxic nature of a patient's cancer can guide and greatly affect the therapeutic regimen and outcome.

In one aspect, there is provided a compound comprising the formula I or a pharmaceutically acceptable salt thereof:

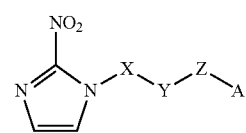

wherein:

X is a ($C_1$-$C_{10}$)alkylenyl, unsubstituted or substituted with 1, 2, 3 or 4 $X^1$, wherein one of the ($C_1$-$C_{10}$)alkylenyl carbon atoms is optionally replaced by a group selected from —CO—, —CONR'—, —NR'CO—, —NR'—, —O— and —S—, or wherein 2, 3 or 4 contiguous atoms of the ($C_1$-$C_{10}$) alkylenyl group form an unsubstituted or substituted ($C_3$-$C_8$) cycloalkyl or a ($C_3$-$C_8$)heterocycloalkyl ring, unsubstituted or substituted with 1, 2, 3 or 4 $X^1$, or a combination thereof;

each $X^1$ is independently hydroxyl, thiol, amino, alkyl, alkoxy, thioalkyl, or halo;

Y is a triazolyl of the formula;

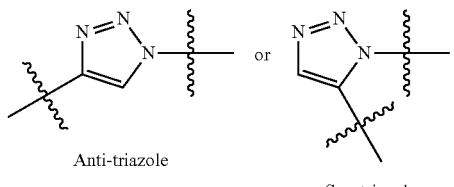

Anti-triazole

Syn-triazole

Z is an ($C_1$-$C_{10}$)alkylenyl group wherein one of the carbon atoms is optionally replaced by a group selected from —CO—, —CONR"—, —NR"CO—, —NR"—, —O— and —S—, and wherein the ($C_1$-$C_{10}$)alkylenyl group is unsubstituted or substituted with 1, 2, 3 or 4 $X^1$;

A is a radioactive element; and R' and R" are each independently H or are each independently selected from the group consisting of (C$_1$-C$_6$)alkyl, —CO(C$_1$-C$_3$)alkyl, —CONH(C$_1$-C$_3$)alkyl and —CO$_2$(C$_1$-C$_3$)alkyl.

In one variation of the above, X is a (C$_1$-C$_4$)alkylenyl group optionally substituted with 1, 2 or 3 hydroxyl groups or 1, 2 or 3 —NH$_2$ or —NH(C$_1$-C$_4$)alkyl group. In another variation, X is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH$_2$—CH(OH)—CH$_2$—, —CH$_2$—CH$_2$—CH(OH)— and —CH$_2$—CH(OH)—CH(OH)—CH$_2$—. In a particular variation, X is selected from the group consisting of —CONR'—, —(C$_1$-C$_4$)alkylCONR'—, —CONR'(C$_1$-C$_4$)alkyl-, —(C$_1$-C$_4$)alkyl-CONR'(C$_1$-C$_4$)alkyl, wherein R' is H or (C$_1$-C$_3$)alkyl. In a particular variation of the above compound, any one of X, Z or A comprises of a $^{11}$C.

In another aspect, there is provided a compound of the formula II or a pharmaceutically acceptable salt thereof or formula III or a pharmaceutically acceptable salt thereof

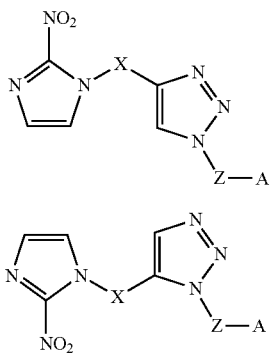

wherein X is a (C$_1$-C$_{10}$)alkylenyl, unsubstituted or substituted with 1, 2, 3 or 4 X$^1$, wherein one of the (C$_1$-C$_{10}$)alkylenyl carbon atoms is optionally replaced by a group selected from —CO—, —CONR'—, —NR'CO—, —NR'—, —O— and —S—, or wherein 2, 3 or 4 contiguous atoms of the (C$_1$-C$_{10}$)alkylenyl group form an unsubstituted or substituted (C$_3$-C$_8$)cycloalkyl or a (C$_3$-C$_8$)heterocycloalkyl ring, unsubstituted or substituted with 1, 2, 3 or 4 X$^1$, or a combination thereof;

each X$^1$ is independently selected from the group consisting of hydroxyl, thiol, amino, alkyl, alkoxy, thioalkyl and halo;

Z is an (C$_1$-C$_{10}$)alkylenyl group wherein one of the carbon atoms is optionally replaced by a group selected from —CO—, —CONR"—, —NR"CO—, —NR"—, —O— and —S—, are unsubstituted or substituted with 1, 2, 3 or 4 X$^1$;

A is a radioactive element; and

R' and R" are each independently H or are each independently selected from the group consisting of (C$_1$-C$_6$)alkyl, —CO(C$_1$-C$_3$)alkyl, —CONH(C$_1$-C$_3$)alkyl and —CO$_2$(C$_1$-C$_3$)alkyl.

In one particular embodiment, there is provided a compound comprising the formula IIb or a pharmaceutically acceptable salt thereof:

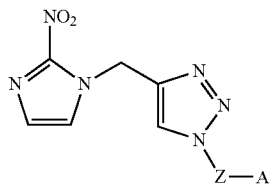

wherein:

Z is an (C$_1$-C$_{10}$)alkylenyl group wherein one of the carbon atoms of the (C$_1$-C$_{10}$)alkylenyl group is optionally replaced by a group selected from —CO—, —CONR"—, —NR"CO—, —NR"—, —O— and —S—, and the (C$_1$-C$_{10}$) alkylenyl group is unsubstituted or substituted with 1, 2, 3 or 4 X$^1$;

R" is H or is selected from the group consisting of (C$_1$-C$_6$)alkyl, —CO(C$_1$-C$_3$)alkyl, —CONH(C$_1$-C$_3$)alkyl and —CO$_2$(C$_1$-C$_3$)alkyl;

each X$^1$ is independently hydroxyl, thiol, amino, alkyl, alkoxy, thioalkyl or halo; and A is a radioactive element.

In a particular variation according to each of the above, Z is an (C$_1$-C$_4$)alkylenyl group optionally substituted with 1, 2 or 3 groups independently selected from the group consisting of hydroxyl, thiol, amino, (C$_1$-C$_4$)alkyl, (C$_1$-C$_4$)alkoxy, thio(C$_1$-C$_4$)alkyl and halo. In one variation of the above compound, Z is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH(CH$_2$OH)—CH$_2$—, —CH$_2$—CH(OH)—CH$_2$—, —CH$_2$—CH$_2$—CH(OH)— and —CH$_2$—CH(OH)—CH(OH)—CH$_2$—.

In a variation according to each of the above, A is $^{18}$F or $^{11}$C-Me. In a particular variation of the above, A is $^{18}$F. In one variation of the above, there is provided a compound of the formula:

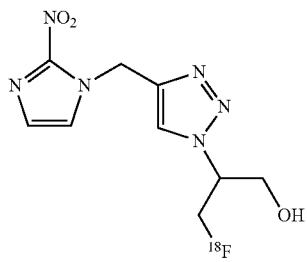

or a pharmaceutically acceptable salt thereof.

In another embodiment, there is provided a compound comprising the formula IV or a pharmaceutically acceptable salt thereof:

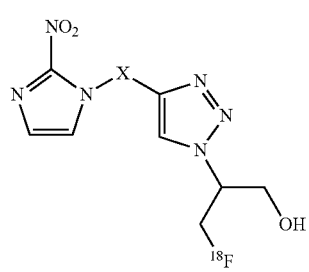

wherein:

X is a $(C_1-C_{10})$alkylenyl, unsubstituted or substituted with 1, 2, 3 or 4 $X^1$, wherein one of the $(C_1-C_{10})$alkylenyl carbon atoms is optionally replaced by a group selected from —CO—, —CONR'—, —NR'CO—, —NR'—, —O— and —S—, or wherein 2, 3 or 4 contiguous atoms of the $(C_1-C_{10})$ alkylenyl group form an unsubstituted or substituted $(C_3-C_8)$ cycloalkyl or a $(C_3-C_8)$heterocycloalkyl ring, unsubstituted or substituted with 1, 2, 3 or 4 $X^1$, or a combination thereof;

R' is H or is selected from the group consisting of $(C_1-C_6)$alkyl, —CO$(C_1-C_3)$alkyl, —CONH$(C_1-C_3)$alkyl and —CO$_2(C_1-C_3)$alkyl; and each $X^1$ is independently selected from the group consisting of hydroxyl, thiol, amino, $(C_1-C_4)$alkyl, $(C_1-C_4)$alkoxy, thio$(C_1-C_4)$alkyl and halo.

In a particular variation of the above compound, X is $(C_1-C_5)$alkylenyl, unsubstituted or substituted with 1 or 2 $X^1$, or wherein one of the $(C_1-C_{10})$alkylenyl carbon atoms is optionally replaced by a group selected from —CONR'— or —NR'CO—, or wherein 2, 3 or 4 contiguous atoms of the $(C_1-C_{10})$alkylenyl group form an unsubstituted or substituted $(C_3-C_8)$cycloalkyl unsubstituted or substituted with 1, 2 or 3 $X^1$, wherein $X^1$ is —OH or NH$_2$.

In another embodiment, there is provided a compound comprising the formula V or a pharmaceutically acceptable salt thereof:

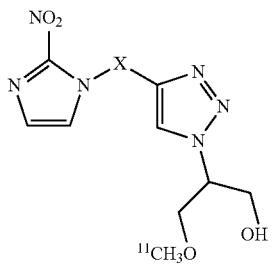

V wherein:

X is a $(C_1-C_{10})$alkylenyl, unsubstituted or substituted with 1, 2, 3 or 4 $X^1$, wherein one of the $(C_1-C_{10})$alkylenyl carbon atoms is optionally replaced by a group selected from —CO—, —CONR'—, —NR'CO—, —NR'—, —O— and —S—, or wherein 2, 3 or 4 contiguous atoms of the $(C_1-C_{10})$ alkylenyl group form an unsubstituted or substituted $(C_3-C_8)$ cycloalkyl or a $(C_3-C_8)$heterocycloalkyl ring, unsubstituted or substituted with 1, 2, 3 or 4 $X^1$, or a combination thereof;

R' is H or is selected from the group consisting of $(C_1-C_6)$ alkyl, —CO$(C_1-C_3)$alkyl, —CONH$(C_1-C_3)$alkyl and —CO$_2(C_1-C_3)$alkyl; and each $X^1$ is independently selected from the group consisting of hydroxyl, thiol, amino, alkyl, alkoxy, thioalkyl and halo.

In a particular variation of the above, there is provided a compound comprising the formula

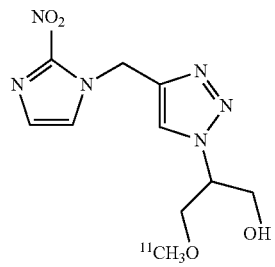

or a pharmaceutically acceptable salt thereof.

In another aspect of the above compounds, there is provided the following compounds:

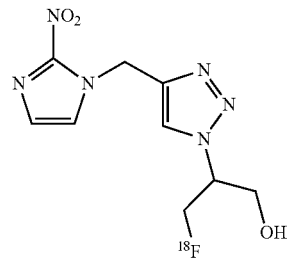

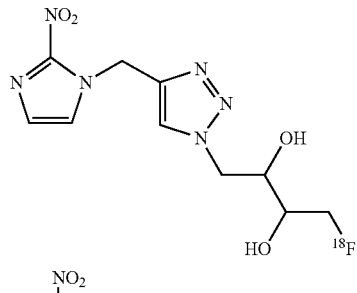

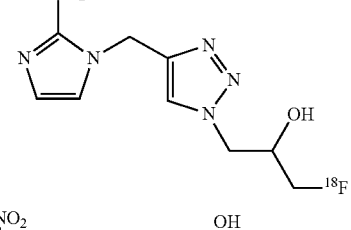

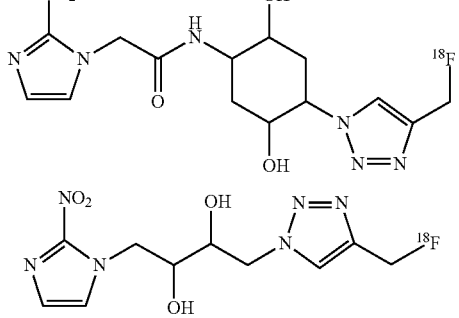

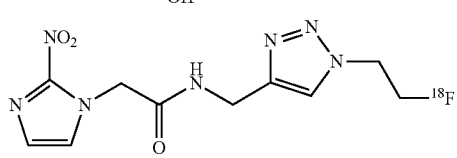

-continued

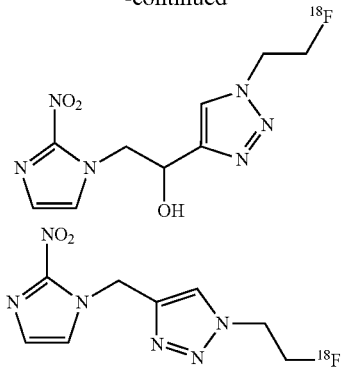

or a pharmaceutically acceptable salt of these compounds.

In another embodiment, there is provided a method for detecting hypoxia in cells comprising: a) administering to a mammal a compound comprising the formula I or a pharmaceutically acceptable salt thereof:

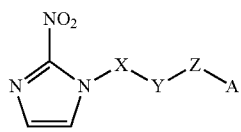

I wherein X is a $(C_1-C_{10})$alkylenyl, unsubstituted or substituted with 1, 2, 3 or 4 $X^1$, wherein one of the $(C_1-C_{10})$ alkylenyl carbon atoms is optionally replaced by a group selected from —CO—, —CONR'—, —NR'CO—, —NR'—, —O— and —S—, or wherein 2, 3 or 4 contiguous atoms of the $(C_1-C_{10})$alkylenyl group form an unsubstituted or substituted $(C_3-C_8)$cycloalkyl or a $(C_3-C_8)$heterocycloalkyl ring, unsubstituted or substituted with 1, 2, 3 or 4 $X^1$, or a combination thereof;

each $X^1$ is independently selected from the group consisting of hydroxyl, thiol, amino, alkyl, alkoxy, thioalkyl and halo;

Y is a triazolyl of the formula;

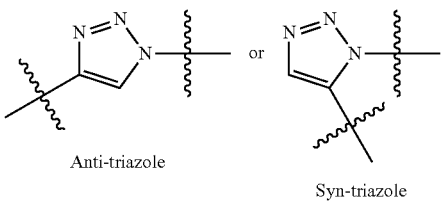

Anti-triazole    Syn-triazole

Z is an $(C_1-C_{10})$alkylenyl group wherein one of the carbon atoms of the $(C_1-C_{10})$alkylenyl group is optionally replaced by a group selected from —CO—, —CONR'—, —NR'CO—, —O— and —S—, and the $(C_1-C_{10})$alkylenyl group is unsubstituted or substituted with 1, 2, 3 or 4 $X^1$;

A is a radioactive element; and

R' and R" are each independently H or are each independently selected from the group consisting of $(C_1-C_6)$alkyl, —CO($C_1-C_3$)alkyl, —CONH($C_1-C_3$)alkyl and —CO$_2$($C_1$-$C_3$)alkyl; and b) detecting by PET the presence of retained radioactive element in hypoxic cells of the mammal.

In a particular variation of the above method, X is a $(C_1-C_4)$alkylenyl group optionally substituted with 1, 2 or 3 hydroxyl groups or 1, 2 or 3 —NH$_2$ or —NH($C_1$-$C_4$)alkyl group. In another variation of the above, X is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH$_2$—CH(OH)—CH$_2$—, —CH$_2$—CH$_2$—CH(OH)— and —CH$_2$—CH(OH)—CH(OH)—CH$_2$—. In another variation of the above method, X is selected from the group consisting of —CONR'—, —($C_1$-$C_4$)alkylCONR'—, —CONR'($C_1$-$C_4$)alkyl- and —($C_1$-$C_4$)alkylCONR'($C_1$-$C_4$)alkyl-, and wherein R' is H or ($C_1$-$C_3$)alkyl.

In one particular variation of the above method, the compound is of formula II or III or a pharmaceutically acceptable salt thereof

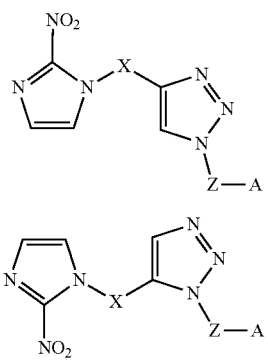

II

III wherein:

X is a $(C_1-C_{10})$alkylenyl, unsubstituted or substituted with 1, 2, 3 or 4 $X^1$, wherein one of the $(C_1-C_{10})$alkylenyl carbon atoms is optionally replaced by a group selected from —CO—, —CONR'—, —NR'CO—, —O— and —S—, or wherein 2, 3 or 4 contiguous atoms of the $(C_1-C_{10})$alkylenyl group form an unsubstituted or substituted $(C_3-C_8)$cycloalkyl or a $(C_3-C_8)$heterocycloalkyl ring, unsubstituted or substituted with 1, 2, 3 or 4 $X^1$, or a combination thereof;

each $X^1$ is independently selected from the group consisting of hydroxyl, thiol, amino, alkyl, alkoxy, thioalkyl and halo;

Z is an $(C_1-C_{10})$alkylenyl group wherein one of the carbon atoms of the $(C_1-C_{10})$alkylenyl group is optionally replaced by a group selected from —CO—, —CONR"—, —NR"CO—, —NR"—, —O— and —S—, and the $(C_1-C_{10})$alkylenyl group is unsubstituted or substituted with 1, 2, 3 or 4 $X^1$;

A is a radioactive element; and R' and R" are each independently H or are each independently selected from the group consisting of $(C_1-C_6)$alkyl, —CO($C_1-C_3$)alkyl, —CONH($C_1-C_3$)alkyl and —CO$_2$($C_1-C_3$)alkyl.

In one variation of the above method, the compound is of the formula II. In another variation of each of the above method, Z is $(C_1-C_4)$alkylenyl group optionally substituted with 1, 2 or 3 hydroxyl groups or 1, 2 or 3 hydroxy($C_1-C_4$) alkyl groups. In one particular variation of the above method, Z is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH(CH$_2$OH)—CH$_2$—, —CH$_2$—CH(OH)—CH$_2$—, —CH$_2$—CH$_2$—CH(OH)— and —CH$_2$—CH(OH)—CH(OH)—

CH$_2$—. In a particular variation of each of the above methods, A is $^{18}$F or $^{11}$C-Me. In another particular variation of the method, A is $^{18}$F.

In one variation of the above method, the compound comprises the formula:

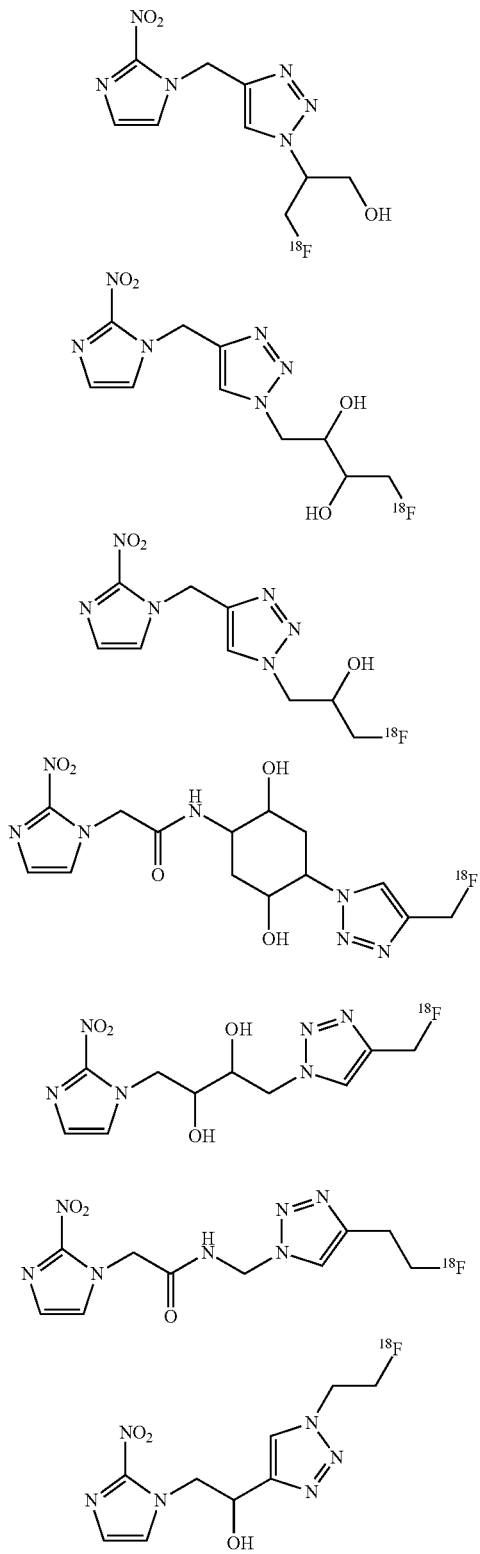

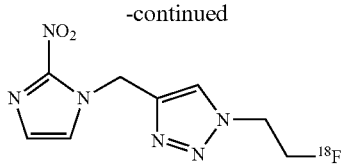

or a pharmaceutically acceptable salt of the preceding compounds.

In a particular aspect of the above method, the hypoxic cells are tumor cells or ischemic cells.

In another embodiment, there is provided a method of preparing a compound of formula II or III, or a mixture thereof:

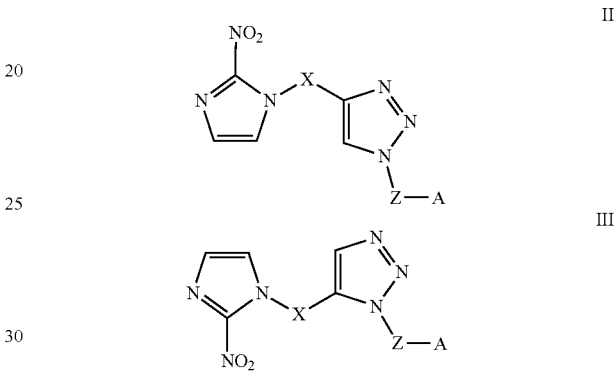

wherein, X is a (C$_1$-C$_{10}$)alkylenyl, unsubstituted or substituted with 1, 2, 3 or 4 X$^1$, wherein one of the (C$_1$-C$_{10}$) alkylenyl carbon atoms is optionally replaced by a group selected from —CO—, —CONR'—, —NR'CO—, —NR'—, —O— and —S—, or wherein 2, 3 or 4 contiguous atoms of the (C$_1$-C$_{10}$)alkylenyl group form an unsubstituted or substituted (C$_3$-C$_8$)cycloalkyl or a (C$_3$-C$_8$)heterocycloalkyl ring, unsubstituted or substituted with 1, 2, 3 or 4 X$^1$, or a combination thereof each X$^1$ is independently selected from the group consisting of hydroxyl, thiol, amino, alkyl, alkoxy, thioalkyl and halo;

Z is an (C$_1$-C$_{10}$)alkylenyl group wherein one of the carbon atoms of the (C$_1$-C$_{10}$)alkylenyl group is optionally replaced by a group selected from —CO—, —CONR"—, —NR"CO—, —NR"—, —O— and —S—, and the (C$_1$-C$_{10}$) alkylenyl group is unsubstituted or substituted with 1, 2, 3 or 4 X$^1$;

A is a radioactive element; and

R' and R" are each independently H or are each independently selected from the group consisting of (C$_1$-C$_6$)alkyl, —CO(C$_1$-C$_3$)alkyl, —CONH(C$_1$-C$_3$)alkyl and —CO$_2$(C$_1$-C$_3$)alkyl; the method comprising:

a) treating an azide substituted compound A'-Z—N$_3$ with an acetylene substituted nitroimidazole, wherein A' is a leaving group; and

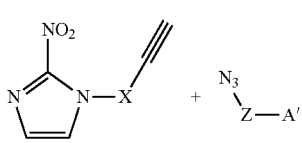

b) radiolabeling the product of step a) by the displacement of A' with a radiolabeling agent to form compound II or III or a mixture thereof, wherein A is either $^{18}$F or $^{11}$C.

In one variation of the above, the compound is of the formula

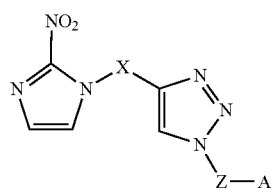

II or a pharmaceutically acceptable salt thereof

In a particular variation of the above method, the radiolabeling agent is K$^{18}$F.

IN THE DRAWINGS

FIG. 1. Bio-distribution of Compound 1 in male white mouse 120 min post IV injection (200 µl of a 5 mM solution).

FIG. 2. Plasma and Urine Pharmacology Study of Compound 1 in Wild-type Rat (1 ml at 10 mM concentration).

Figure 3:
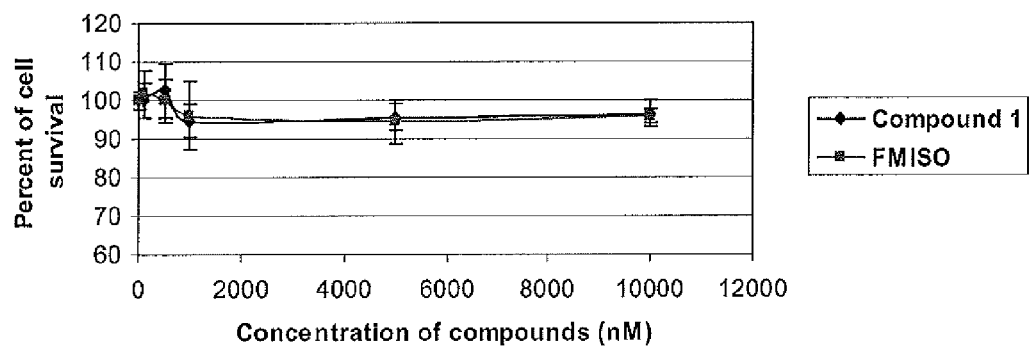

FIG. 3, Cytotoxicity Assay (A172 cells incubated with different concentration of compounds)

Figure 4:
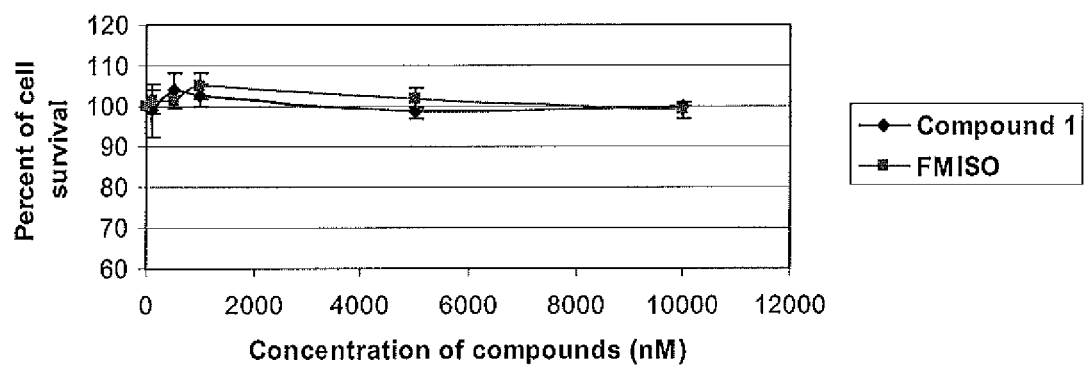

FIG. 4. Cytotoxicity Assay (LS174T cells incubated with different concentration of compounds).

Figure 5:
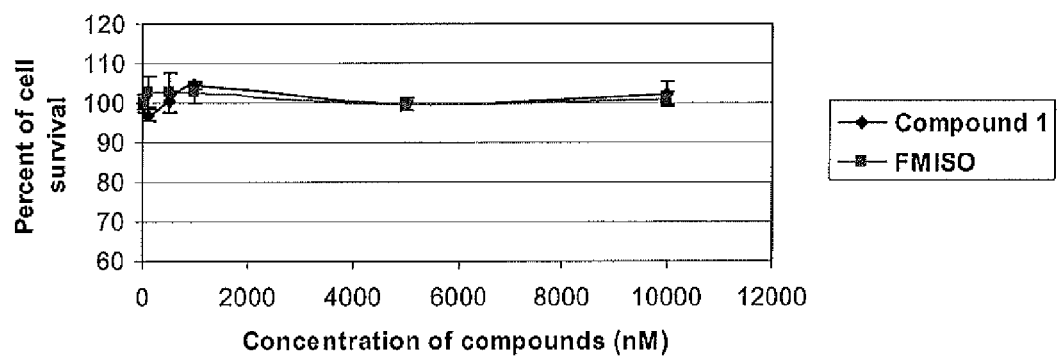

FIG. 5. Cytotoxicity Assay (AML12 cells incubated with different concentration of compounds).

FIG. 6. PET Images.

DETAILED DESCRIPTION OF THE INVENTION

The present invention will now be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

The novel compounds described herein contain the requisite 2-nitroimidazole core that is necessary for imaging hypoxic tumors. Without being bound by theory, mechanistically, intracellular bioreduction under hypoxic conditions modifies the 2-nitroimidazole core which then undergoes covalently-mediated localization within the cell. Under oxic conditions, the bioreduced nitroimidazole returns to its native state and diffuses freely into and out of the cell.

The novel compounds disclosed herein also display favorable imaging pharmacokinetic properties. The compounds possess favorable clearance properties via renal excretion, thus exhibiting lower uptake in the liver and gut regions. These compounds also clear quickly from both blood and muscle tissue, thus leading to desirable tumor to background ratios. In addition, these favorable clearance properties translate into peak tumor to background ratios at a timepoint earlier than the "gold standard" [$^{18}$F]F-MISO. These tracers are highly selective for hypoxic tumors over non-hypoxic tumors. In xenograph mice and rats, the tracer preferentially localizes within hypoxic tumors and, in most cases, with tumor to background ratios greater than 2:1.

This class of compounds appears to be benign on the cellular level in that, for example, Compound 1 exhibits no cytotoxic effects in either normal human or cancer cells at concentrations up to 10,000 nM.

DEFINITIONS

As used herein, the singular forms "a", "an", "the", include plural referents unless the context clearly dictates otherwise.

"Alkyl" refers to a hydrocarbon chain, typically ranging from about 1 to 20 atoms in length. Such hydrocarbon chains may be branched or straight chain, although typically straight chain is preferred. Exemplary alkyl groups include ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Alkylenyl" refers to a hydrocarbon chain, typically ranging from about 1 to 20 atoms in length, or 1 to 10 carbon atoms in length, that is divalently bonded to two different groups. Such hydrocarbon chains may be branched or straight chain. Exemplary alkylenyl groups include ethylenyl, propylenyl, iso-propylenyl, butylenyl, iso-butylenyl, pentylenyl, 1-methylbutylenyl, 1-ethylpropylenyl, 3-methylpentylenyl, and the like, wherein the divalent bonds may be at any of the carbon atoms of the alkylenyl group, or as specifically indicated. As used herein, "alkylenyl" also includes cycloalkylenyl when three or more carbon atoms are referenced.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

A "biological target" can be any biological molecule involved in biological pathways associated with any of various diseases and conditions, including cancer (e.g., leukemia, lymphomas, brain tumors, breast cancer, lung cancer, prostate cancer, gastric cancer, as well as skin cancer, bladder cancer, bone cancer, cervical cancer, colon cancer, esophageal cancer, eye cancer, gallbladder cancer, liver cancer, kidney cancer, laryngeal cancer, oral cancer, ovarian cancer, pancreatic cancer, penile cancer, glandular tumors, rectal cancer, small intestine cancer, sarcoma, testicular cancer, urethral cancer, uterine cancer, and vaginal cancer), diabetes, neurodegenerative diseases, cardiovascular diseases, respiratory diseases, digestive system diseases, infectious diseases, inflammatory diseases, autoimmune diseases, and the like. Exemplary biological pathways include, for example, cell cycle regulation (e.g., cellular proliferation and apoptosis), angiogenesis, signaling pathways, tumor suppressor pathways, inflammation (COX-2), oncogenes, and growth factor receptors. The biological target may also be referred to as the "target biomacromolecule" or the "biomacromolecule." The biological target can be a receptor, such as enzyme receptors, ligand-gated ion channels, G-protein-coupled receptors, and transcription factors. The biological target is preferably a protein or protein complex, such as enzymes, membrane transport proteins, hormones, and antibodies.

"Contiguous atoms" means atoms that are adjacent to each other. For example, the phrase "2, 3 or 4 contiguous atoms of the (C$_1$-C$_{10}$)alkylenyl group form an unsubstituted or substituted (C$_3$-C$_8$)cycloalkyl or a (C$_3$-C$_8$)heterocycloalkyl ring" means that the 2, 3 or 4 adjacent atoms in an alkylenyl group or a linker, for example, form part of a (C$_3$-C$_8$)cycloalkyl or a (C$_3$-C$_8$)heterocycloalkyl ring. For example, for the 3 contiguous carbon atoms represented in Fragment "A" below, when the atoms form an unsubstituted (C$_3$-C$_8$)cycloalkyl group such as a cyclohexyl group, the fragment may form as shown in Fragment "B."

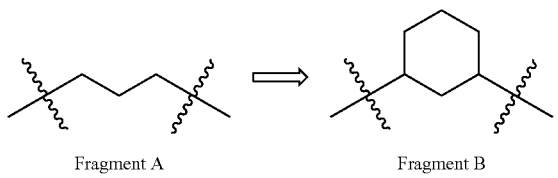

Fragment A    Fragment B

"Cycloalkyl" refers to a saturated, partially unsaturated or unsaturated cyclic hydrocarbon chain, including bridged, fused, or Spiro cyclic rings, preferably made up of 3 to about 12 carbon atoms, more preferably 3 to 8 carbon atoms.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 3-12 atoms, preferably 5-7 atoms, with or without unsaturation or aromatic character, and having at least one ring atom which is not a carbon. Preferred heteroatoms include sulfur, oxygen, and nitrogen.

"Leaving group", as used herein refers to groups that are readily displaced, for example, by a nucleophile, such as an amine, a thiol or an alcohol nucleophile or its salt. Such leaving groups are well known and include, for example carboxylates, N-hydroxysuccinimide, N-hydroxybenzotriazole, halides, triflates, tosylates, nosylates, —OR and —SR and the like.

"Linker" as used herein refers to a chain comprising 1 to 10 atoms and may comprise of 1, 2 or 3 adjacent or non-adjacent atoms or groups, such as C, —NR—, O, S, —S(O)—, —S(O)$_2$—, CO, —C(NR)— and the like, and wherein R is H or is selected from the group consisting of (C$_{1-10}$)alkyl, (C$_{3-8}$)cycloalkyl, aryl(C$_{1-5}$)alkyl, heteroaryl(C$_{1-5}$)alkyl, amino, aryl, heteroaryl, hydroxy, (C$_{1-10}$)alkoxy, aryloxy, heteroaryloxy, each substituted or unsubstituted. That is, for example, the linker may comprise of the groups: —CH$_2$—, —CH$_2$—CH$_2$—, —CH$_2$—O—CH$_2$—, —CH$_2$—CH$_2$—O—CH$_2$—CH$_2$—, —CH$_2$—NH—CH$_2$—, —CH$_2$—CH$_2$—NH—CH$_2$—CH$_2$—, —CH$_2$—NHC(O)—CH$_2$—, —CH$_2$—C(O)NH—CH$_2$—, —CH$_2$—C(O)—CH$_2$— etc. . . . The linker chain may also comprise part of a saturated, unsaturated or aromatic ring, including polycyclic and heteroaromatic rings, in certain aspect of the compounds of the present application, the variables X and Z may be the linker or linker chain. As used herein, the representation of "(C$_{1-3}$)alkyl", for example, is used interchangeably with "C$_1$-C$_4$alkyl" to mean the same.

The terms "patient" and "subject" refer to any human or animal subject, particularly including all mammals.

As used herein, "radiochemical" is intended to encompass any organic, inorganic or organometallic compound comprising a covalently-attached radioactive isotope, any inorganic radioactive ionic solution (e.g., Na[$^{18}$F]F ionic solution), or any radioactive gas (e.g., [$^{11}$C]CO$_2$), particularly including radioactive molecular imaging probes intended for administration to a patient (e.g., by inhalation, ingestion or intravenous injection) for tissue imaging purposes, which are also referred to in the art as radiopharmaceuticals, radiotracers or radioligands. Although the present invention is primarily directed to synthesis of positron-emitting molecular imaging probes for use in PET imaging systems, the invention could be readily adapted for synthesis of any radioactive compound comprising a radionuclide, including radiochemicals useful in other imaging systems, such as single photon emission computed tomography (SPECT).

As used herein, the term "radioactive isotope" or "radioactive element" refers to isotopes exhibiting radioactive decay (i.e., emitting positrons) and radiolabeling agents comprising a radioactive isotope (e.g., [$^{11}$C]methane, [$^{11}$C]carbon monoxide, [$^{11}$C]carbon dioxide, [$^{11}$C]phosgene, [$^{11}$C] urea, [$^{11}$C]cyanogen bromide, as well as various acid chlorides, carboxylic acids, alcohols, aldehydes, and ketones containing carbon-11). Such isotopes or elements are also referred to in the art as radioisotopes or radionuclides. Radioactive isotopes are named herein using various commonly used combinations of the name or symbol of the element and its mass number (e.g., $^{18}$F, F-18, or fluorine-18). Exemplary radioactive isotopes include I-124, F-18 fluoride, C-11, N-13, and O-15, which have half-lives of 4.2 days, 110 minutes, 20 minutes, 10 minutes, and 2 minutes, respectively. The radioactive isotope is preferably dissolved in an organic solvent, such as a polar aprotic solvent. Preferably, the radioactive isotopes used in the present method include F-18, C-11, I-123, I-124, I-127, I-131, Br-76, Cu-64, Tc-99m, Y-90, Ga-67, Cr-51, Ir-192, Mo-99, Sm-153 and Tl-201. Preferably, the radioactive isotope used in the present method is F-18. Other radioactive isotopes that may be employed include: As-72, As-74, Br-75, Co-55, Cu-61, Cu-67, Ga-68, Ge-68, I-125, I-132, In-111, Mn-52, Pb-203 and Ru-97.

"Substituted" or a "substituent" as used herein, means that a compound or functional group comprising one or more hydrogen atom of which is substituted by a group (a substituent) such as a —C$_{1-5}$alkyl, C$_{2-5}$alkenyl, halogen or halo (chlorine, fluorine, bromine, iodine atom), —CF$_3$, nitro, amino (—NH$_2$, —NHR, —NR$_2$, etc. . . . ), oxo (i.e., forming —C(=O)—), —OH, carboxyl (—COOH), —COOC$_{1-5}$alkyl, —OC$_{1-5}$alkyl, —CONHC$_{1-5}$ alkyl, —NHCOC$_{1-5}$alkyl, —OSOC$_{1-5}$alkyl, —SO OC$_{1-5}$ alkyl, —SOONHC$_{1-5}$alkyl, —NHSO$_2$C$_{1-5}$alkyl, aryl, heteroaryl and the like, each of which may be further substituted.

"Thioalkyl" means a C$_{1-10}$alkyl-S— group that may be unsubstituted or substituted with a —C$_{1-5}$alkyl, C$_{2-5}$alkenyl, halogen or halo (chlorine, fluorine, bromine, iodine atom), —CF$_3$, nitro, amino (—NH$_2$, —NHR, —NR$_2$, etc. . . . ), oxo (i.e., forming —C(=O)—), —OH, carboxyl, —COOC$_{1-5}$ alkyl, —OC$_{1-5}$alkyl, —CONHC$_{1-5}$alkyl, —NHCOC$_{1-5}$alkyl, —OSOC$_{1-5}$alkyl, —SOO C$_{1-5}$alkyl, —SOONHC$_{1-5}$alkyl, —NHSO$_2$C$_{1-5}$alkyl, aryl and heteroaryl.

"Triazole" as used herein means either 1,3,4- or 1,2,3-triazole, or mixtures thereof. In a preferred embodiment, the "triazole" is a 1,2,3-triazole, substituted in the 1- and 5-positions ("syn") or in the 1- and 4-positions ("anti") or mixtures thereof. In a particularly preferred embodiment, the 1,2,3-triazole is substituted in the 1- and 4-positions.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts.

Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise a compound represented by the various Formulas shown (or pharmaceutically acceptable salts thereof) as an active ingredient, a pharmaceutically acceptable carrier and optionally other therapeutic ingredients or adjuvants.

Click Chemistry Method

Click chemistry provides chemists an opportunity to rapidly produce libraries of candidate imaging agents, from which potential small molecule PET imaging tracers with optimal pharmacodynamic and pharmacokinetic properties may be identified. Click chemistry is a modular approach to chemical synthesis that utilizes only the most practical and reliable chemical transformations. Click chemistry techniques are described, for example, in the following references, which are incorporated herein by reference in their entirety:

1. Kolb, H. C.; Finn, M. G.; Sharpless, K. B. *Angewandte Chemie, International Edition* 2001, 40, 2004-2021.
2. Kolb, H. C.; Sharpless, K. B. *Drug Discovery Today* 2003, 8, 1128-1137.
Rostovtsev, V. V.; Green, L. G.; Fokin, V. V.; Sharpless, K. B. *Angewandte Chemie, International Edition* 2002, 41, 2596-2599.
3. Tornøe, C. W.; Christensen, C.; Meldal, M. *Journal of Organic Chemistry* 2002, 67, 3057-3064.
4. Wang, Q.; Chan, T. R.; Hilgraf, R.; Fokin, V. V.; Sharpless, K. B.; Finn, M. G. *Journal of the American Chemical Society* 2003, 125, 3192-3193.
5. Lee, L. V.; Mitchell, M. L.; Huang, S.-J.; Fokin, V. V.; Sharpless, K. B.; Wong, C.-H. *Journal of the American Chemical Society* 2003, 125, 9588-9589.
6. Lewis, W. G.; Green, L. G.; Grynszpan, F.; Radic, Z.; Carlier, P. R.; Taylor, P.; Finn, M. G.; Barry, K. *Angew. Chem., Int. Ed.* 2002, 41, 1053-1057.
7. Manetsch, R.; Krasinski, A.; Radic, Z.; Raushel, J.; Taylor, P.; Sharpless, K. B.; Kolb, H. C. *Journal of the American Chemical Society* 2004, 126, 12809-12818.
8. Mocharla, V. P.; Colasson, B.; Lee, L. V.; Roeper, S.; Sharpless, K. B.; Wong, C.-H.; Kolb, H. C. *Angew. Chem. Int. Ed.* 2005, 44, 116-120.
9. M. Whiting, J, Muldoon, Y.-C. Lin, S. M. Silverman, W. Lindstrom, A. J. Olson, H. C. Kolb, M. G. Finn, K. B. Sharpless, J. H. Elder, V. V. Fokin, *Angew. Chem.* 2006, 118, 1463-1467; *Angew. Chem. Int. Ed. Engl.* 2006, 45, 1435-1439.

Although other click chemistry functional groups can be utilized, such as those described in the above references, the use of cycloaddition reactions is preferred, particularly the reaction of azides with alkynyl groups. Alkynes, such as terminal alkynes, and azides undergo 1,3-dipolar cycloaddition forming 1,4-disubstituted 1,2,3-triazoles. Alternatively, a 1,5-disubstituted 1,2,3-triazole can be formed using azide and alkynyl reagents (Krasinski, A., Fokin, V. V. & Barry, K. *Organic Letters* 2004, 1237-1240). Hetero-Diels-Alder reactions or 1,3-dipolar cycloaddition reactions could also be used (see Huisgen 1,3-*Dipolar Cycloaddition Chemistry* (Vol. 1) (Padwa, A., ed.), pp. 1-176, Wiley; Jorgensen *Angew. Chem. Int. Ed. Engl.* 2000, 39, 3558-3588; Tietze, L. F. and Kettschau, G. *Top. Curr. Chem.* 1997, 189, 1-120). In one particular embodiment, the click chemistry method as provided herein provides novel compounds that are further incorporated with a PET label.

The entire disclosures of all documents cited throughout this application are incorporated herein by reference.

Experimentals

Outlined below are the general procedures for the synthesis of the compounds of formulae II and III:

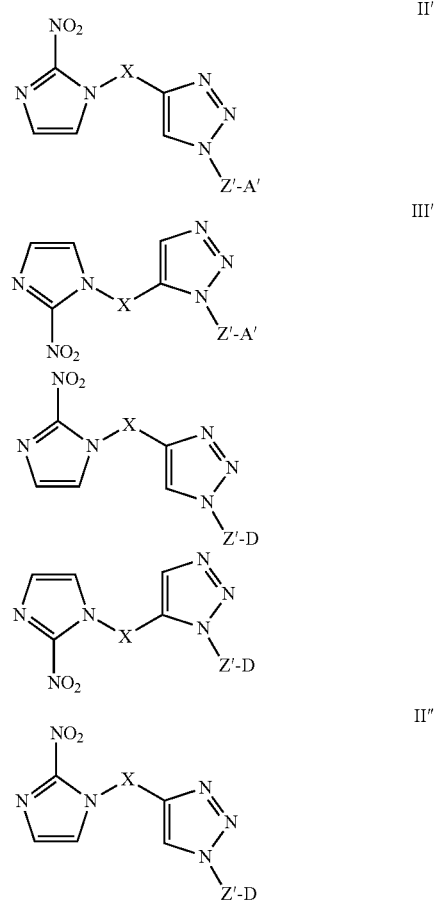

-continued

III''

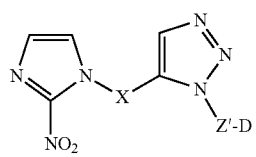

General scheme for the synthesis of 1,5-disubstituted ("syn") triazoles:

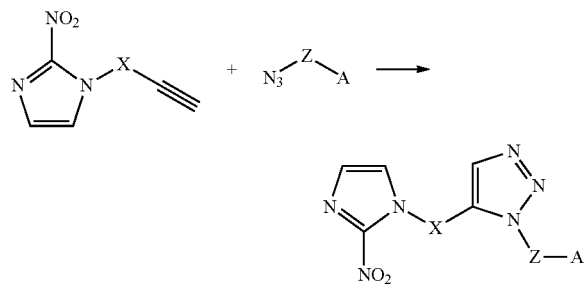

General scheme for the synthesis of 1,4-disubstituted ("anti") triazoles:

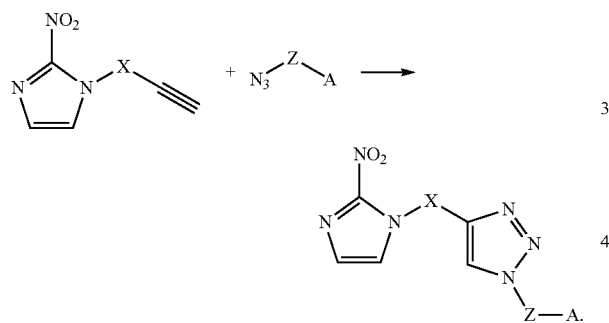

As depicted in the above general schemes, where A is a group, such as an alkyl group, comprising a leaving group or where A is a leaving group, then the triazole comprising a radioactive isotope or radioactive element may be prepared by the displacement or substitution of A with the radioactive isotope or the radioactive element, as disclosed herein.

General Experimental Conditions:

All reactions were carried out in oven dried glassware under an atmosphere of Ar. Gradient conditions for normal phase purification using silica gel cartridges are listed below for EtOAc:Hex mixtures. The duration of the run is given in column volumes (cv). The detection wavelength was set at 254 nm. Solvents for reactions were purchased as anhydrous grade and used without further purification.

| Duration (cv) | 0 | 1.8 | 19.6 | 5.4 | 0 | 1.8 |
|---|---|---|---|---|---|---|
| % EtOAc | 0 | 0 | 100 | 100 | 0 | 0 |

Preparation of Compounds 8 and 12:

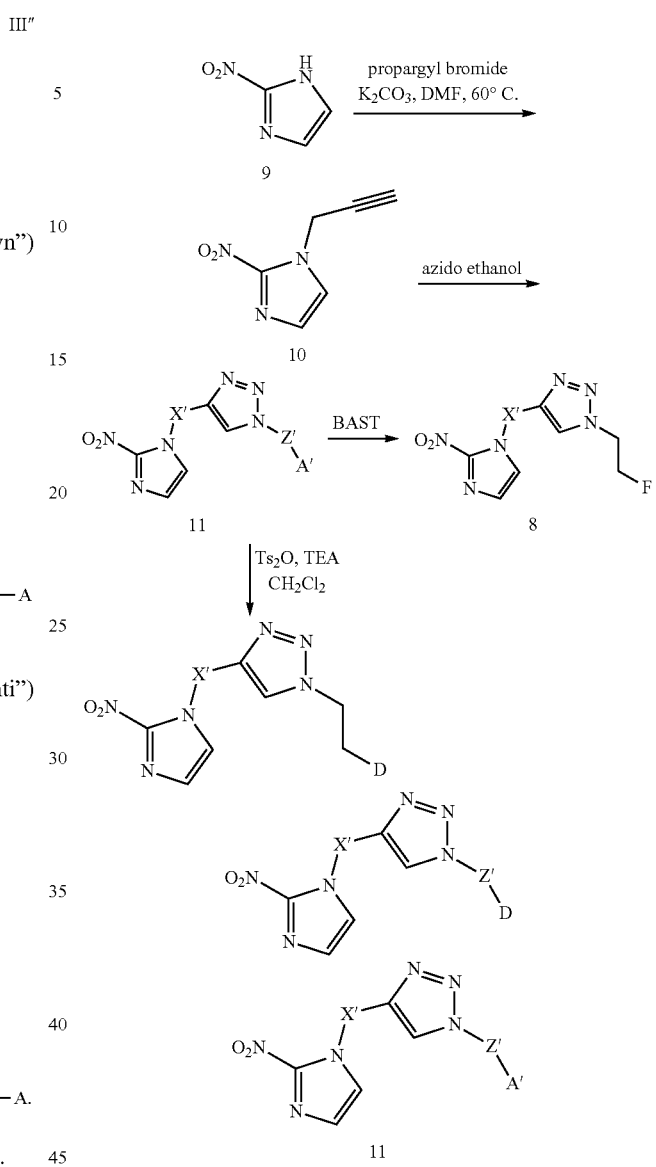

2-Nitro-1-(prop-2-ynyl)-1H-imidazole (10): To a round bottom flask was added 2-nitroimidazole (500 mg, 4.42 mmol), propargyl bromide (631 mg, 5.31 mmol), potassium carbonate (733 mg, 5.31 mmol) and DMF (5 mL). The reaction was stirred overnight at RT. TLC (EtOAc) indicated complete reaction. The reaction was poured onto water (20 mL) and extracted into EtOAc (3×20 mL). The combined organics were washed with water (5×20 mL). The organic layer was then concentrated in vacuo and purified on a silica gel cartridge using EtOAc:Hex as the eluent to afford 571 mg (85% yield) of 10 as a pale yellow solid. $^1$H NMR (CDCl$_3$, 400 MHz), δ: 2.63 (1H, d, J=5.6 Hz), 5.23 (2H, d, J=2.4 Hz), 7.20 (1H, d, J=1.2 Hz), 7.46 (1H, s). Mass Spec (lo-res): Calc'd for C$_6$H$_5$N$_3$O$_2$: 151.04; found: 152.10 (M+H).

2-(4-((2-Nitro-1H-imidazol-1-yl)methyl)-1H-1,2,3-triazol-1-yl)ethanol (11): To a round bottom flask was added nitropropyne 10 (150 mg, 0.99 mmol) and azido ethanol (86 mg, 0.99 mmol). To this flask was added CuSO$_4$ (0.04M, 100 uL) and sodium ascorbate (0.1 M, 100 uL). After 16 hrs, the reaction was poured onto EtOAc and washed with NH$_4$OH.

The organics were combined and the residue was purified on a combiflash system using EtOAc:Hex as the eluent followed by DCM:MeOH to afford 180 mg (76.3% yield) of 11 as a clear colorless oil. Mass Spec (lo-res): Calc'd for $C_8H_{14}N_6O_3$: 238.08; found: 239.10 (M+H).

2-(4-((2-Nitro-1H-imidazol-1-yl)methyl)-1H-1,2,3-triazol-1-yl)ethanol (11): To a round bottom flask is added nitropropyne 10 (150 mg, 0.99 mmol) and azido ethanol (86 mg, 0.99 mmol). The reaction is stirred overnight at 60° C. The residue is purified on a combiflash system using EtOAc:Hex as the eluent followed by DCM:MeOH to afford 11 as a clear colorless oil.

1-(2-Fluoroethyl)-4-((2-nitro-1H-imidazol-1-yl)methyl)-1H-1,2,3-triazole (8): To a round bottom flask containing alcohol 11 (20 mg, 0.084 mmol) in DCM (5 mL) at 0° C. was added BAST (20.3 mg, 0.126 mmol). The reaction was stirred at 0° C. for 1 hr. The reaction was concentrated in vacuo and purified on a silica gel cartridge using EtOAc:Hex as the eluent to afford 12 mg (60% yield) of 8 as a clear, colorless oil.

2-(4-((2-Nitro-1H-imidazol-1-yl)methyl)-1H-1,2,3-triazol-1-yl)ethyl 4-methylbenzenesulfonate (12): To a round bottom flask containing alcohol 11 (160 mg, 0.672 mmol), TEA (136 mg, 1.34 mmol) and DCM (5 mL) was added Ts$_2$O (263 mg, 0.806 mmol). The reaction was stirred at RT for 4 hrs. TLC indicated that the reaction was complete. The reaction was concentrated in vacuo and purified on a silica gel cartridge using EtOAc:Hex as the eluent to afford 140 mg (53% yield) of 12 as a pale orange oil. Mass Spec (lo-res): Calc'd for $C_{15}H_{16}N_6O_5S$: 392.092; found: 393.10 (M+H).

Preparation of Compounds 3 and 16:

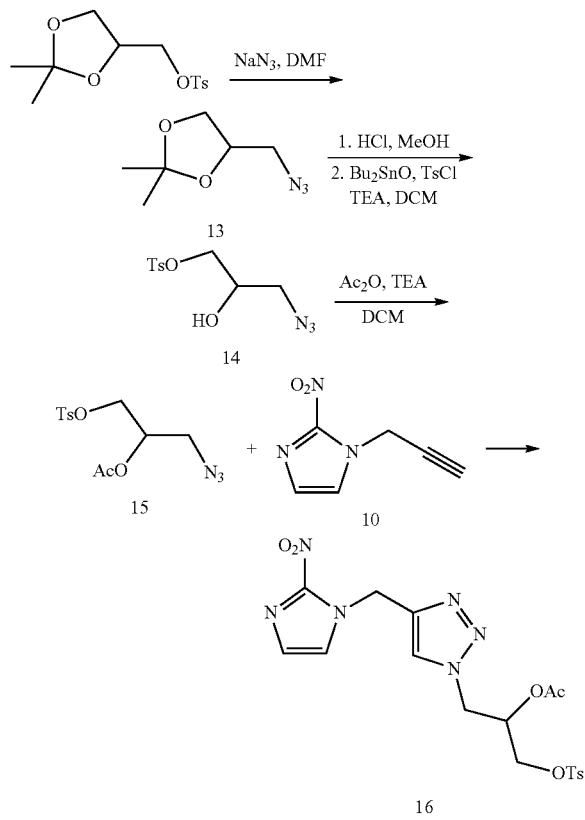

4-(Azidomethyl)-2,2-dimethyl-1,3-dioxolane (13): To a solution of (2,2-dimethyl-1,3-dioxolan-4-yl)methyl 4-methylbenzenesulfonate (5.73 g, 20.00 mmol) in DMF (40 mL) was added sodium azide (2.6 g, 40.00 mmol) and the reaction mixture was stirred at 80° C. for 18 hr. The solvent was evaporated under reduced pressure, diluted with water (100 mL) and extracted 3 times with ethyl acetate (3×75 mL), which was consecutively washed with H$_2$O (100 mL), brine (100 mL) and finally dried over MgSO$_4$. The solvent was removed under vacuum to afford 2.2 g of 13 as brown oil (76% yield). $^1$H NMR (CDCl$_3$, 400 MHz) δ: 4.21-4.27 (m, 1H), 4.02 (dd, J=6.4, 8.4 Hz, 1H), 3.74 (dd, J=6.0, 8.4 Hz, 1H), 3.36 (dd, J=4.8, 12.8 Hz, 1H), 3.26 (dd, J=5.6, 12.8 Hz, 1H), 1.43 (s, 3H), 1.33 (s, 3H).

3-Azido-2-hydroxypropyl 4-methylbenzenesulfonate (14): 4-(Azidomethyl)-2,2-dimethyl-1,3-dioxolane 13 (2.2 g, 13.99 mmol) was dissolved in methanol (25 mL). To this solution was added a solution of HCl in diethyl ether (2M, 5 mL) at 0° C. The mixture was stirred at room temperature overnight, and then concentrated under reduced pressure to afford a yellow oil which was used for the next step without purification. After drying for 0.5 hr, the residue was dissolved in CH$_2$Cl$_2$ (30 mL) and was treated with Bu$_2$SnO (0.071 mg, 0.3 mmol), followed by TsCl (2.86 g, 15.0 mmol) and TEA (2.2 mL, 16 mmol). After stirring for 3 hr at room temperature, water (30 mL) was added and the organic layer was separated. The aqueous layer was extracted with CH$_2$Cl$_2$ (2×50 mL) and the organic layer was consecutively washed with H$_2$O (50 mL) and brine (50 mL) and dried over MgSO$_4$. The solvent was removed under vacuum and the residue was purified on silica gel using 33% EtOAc/hexanes as the eluent to afford 1.86 g of 14 (48% yield) as a clear, colorless oil. $^1$H NMR (CDCl$_3$, 400 MHz) δ: 7.77 (d, J=8.0 Hz, 2H), 7.34 (d, J=8.0 Hz, 2H), 3.96-4.09 (m, 3H), 3.31-3.40 (m, 2H), 2.43 (s, 3H). Mass Spec (lo-res): Calc'd for $C_{10}H_{13}N_3O_4S$: 271.06; found: 294.1 (M+Na$^+$).

1-Azido-3-(tosyloxy)propan-2-yl acetate (15): 3-Azido-2-hydroxypropyl 4-methylbenzenesulfonate 14 (1.83 g, 6.70 mmol) was dissolved in CH$_2$Cl$_2$ (15 mL) and treated with TEA (1.4 mL, 10.00 mmol), a catalytic amount of DMAP and acetic anhydride (0.95 mL, 10.00 mmol) at room temperature. After stirring for 1 hr, silica was added to the reaction mixture, the solvent was evaporated and the residue was purified on silica gel using 50% EtOAc/hexanes as the eluent to afford 2.07 g of 15 (98.8% yield) as a thick, clear, colorless oil. $^1$H NMR (CDCl$_3$, 400 MHz) δ: 7.79 (d, J=8.4 Hz, 2H), 7.37 (d, J=8.0 Hz, 2H), 5.02-5.07 (m, 1H), 4.09-4.21 (m, 2H), 3.43-3.53 (m, 2H), 2.46 (s, 3H), 2.05 (s, 3H). Mass Spec (lo-res): Calc'd for $C_{12}H_{15}N_3O_5S$: 313.07; found: 314.1 (M+H$^+$).

1-(4-((2-Nitro-1H-imidazol-1-yl)methyl)-1H-1,2,3-triazol-1-yl)-3-(tosyloxy)propan-2-yl acetate (16): 2-Nitro-1-(prop-2-ynyl)-1H-imidazole 10 (0.2 g, 1.32 mmol) is heated with 1-azido-3-(tosyloxy)propan-2-yl acetate 15 (0.41 g, 1.32 mmol) at 60° C. overnight. The residue is purified by chromatography on silica gel (MeOH/CH$_2$Cl$_2$, 1:10) to afford 16.

1-(4-((2-Nitro-1H-imidazol-1-yl)methyl)-1H-1,2,3-triazol-1-yl)-3-(tosyloxy)propan-2-yl acetate (16): To a solution of 2-nitro-1-(prop-2-ynyl)-1H-imidazole (0.2 gm, 1.32 mmol) and 1-azido-3-(tosyloxy)propan-2-yl acetate (0.41 gm, 1.32 mmol) in THF (2.5 mL), was treated with CuI (0.025 gm, 0.132 mmol) and DIPEA (0.3 mL, 1.46 mmol) at room temperature. After stirring the reaction mixture for overnight, silica was added, solvent evaporated under reduced pressure and purified by chromatography on silica gel (MeOH/CH$_2$Cl$_2$, 1/10) to give the 1-(4-((2-nitro-1H-imidazol-1-yl)methyl)-1H-1,2,3-triazol-1-yl)-3-(tosyloxy)propan-2-yl acetate (0.5 gm, 81%) as white solid. $^1$H NMR (CDCl$_3$, 400 MHz) δ:

7.76-7.78 (m, 3H), 7.35-7.39 (m, 3H), 7.15 (br, 1H), 5.68 (d, J=5.6 Hz, 2H), 5.27-5.32 (m, 1H), 4.56-4.67 (m, 2H), 4.19 (dd, J=4.0, 11.2 Hz, 1H), 4.08 (dd, J=4.0, 11.2 Hz, 1H), 2.46 (s, 3H), 1.97 (s, 3H); Mass Spec (lo-res): Calc'd for $C_{18}H_{20}N_6O_7S$: 464.11; found: 465.1 (M+H$^+$).

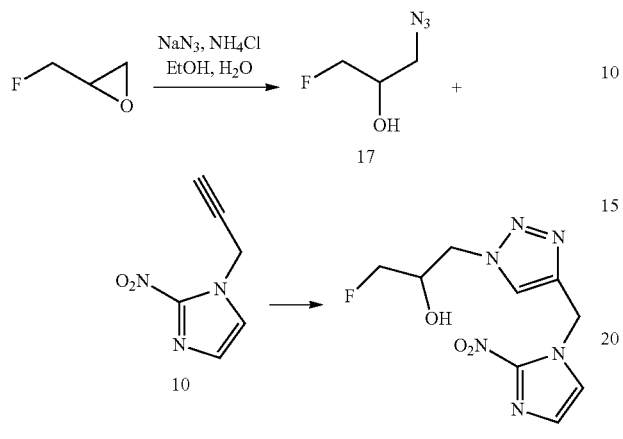

1-Azido-3-fluoropropan-2-ol (17): Epichlorohydrin (13.15 mmol) was dissolved in a mixture of ethanol (10 ml) and water (10 ml). Ammonium chloride (23.6 mmol) was added followed by sodium azide (21.91 mmol). The resulting solution was stirred 50° C. for overnight. The ethanol was removed in vacuo. The mixture was extracted with ethyl acetate (2×50 ml). The organic layer was then concentrated and purified on a silica gel column using EtOAc:Hex as the eluent to afford 740 mg of 17 as a clear, colorless oil. The $^1$H NMR spectrum was consistent with published results.

1-Fluoro-3-(4-((2-nitro-1H-imidazol-1-yl)methyl)-1H-1,2,3-triazol-1-yl)propan-2-ol (3): To a vial was added fluoro-azide 17 (690 mg, 5.79 mmol) and 1-propynyl-2-nitroimidazole (876 mg, 5.79 mmol). To this flask was added THF (3 mL), t-BuOH (3 mL), water (3 mL), CuSO$_4$ (185 mg, 1.16 mmol) and sodium ascorbate (1.15 g, 5.79 mmol). After 16 hrs, the reaction was poured onto EtOAc and washed with NH$_4$OH. The organics were combined and the material was then purified on a silica gel column using EtOAc:Hex as the eluent. The material was then further purified via recrystallization using EtOAc:Hex to afford 65 mg (4% yield) of pale yellow crystals. $^1$H NMR (DMSO-d6, 400 MHz), δ: 4.04 (1H, br d, J=20.4 Hz), 4.20-4.47 (4H, m), 5.53 (1H, br s), 5.66 (2H, s), 7.16, (1H, s), 7.68 (1H, s), 8.05 (1H), s).

1-Fluoro-3-(4-((2-nitro-1H-imidazol-1-yl)methyl)-1H-1,2,3-triazol-1-yl)propan-2-ol (3): To a vial is added fluoro-azide 17 (5.79 mmol) and 1-propynyl-2-nitroimidazole (5.79 mmol). The solution is heated at 60° C. overnight. The material is then purified on a silica gel column using EtOAc:Hex as the eluent. The material is then further purified via recrystallization using EtOAc:Hex to afford pale yellow crystals. Preparation of Compounds 5 and 21:

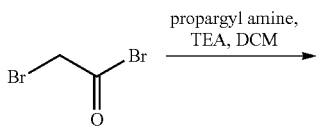

2-Bromo-N-(prop-2-ynyl)acetamide (18): To a round bottom flask containing 2-bromoacetyl bromide (10 g, 49.5 mmol), TEA (5.01 g, 49.5 mmol) and DCM (20 mL) at 0° C., was added dropwise propargyl amine (2.73 g, 49.5 mmol) as a solution in DCM (10 mL) over 1 hr. The reaction stirred overnight at RT. The reaction was poured onto water (20 mL) and washed with sat'd NaHCO$_3$ (1×20 mL). The organic layer was washed with 1N HCl (1×20 mL). The organic layer was concentrated to dryness and purified on a silica gel cartridge using EtOAc:Hex as the eluent to afford 2.44 g (28% yield) of 18 as a pale orange solid. $^1$H NMR (CDCl$_3$, 400 MHz), δ: 2.25 (1H, s), 3.84 (2H, s), 4.05 (2H, s), 6.82 (1H, br s). Mass Spec (lo-res): Calc'd for C$_5$H$_6$BrNO: 174.96; found: 176.00, 178.00 (M+H).

2-(2-Nitro-1H-imidazol-1-yl)-N-(prop-2-ynyl)acetamide (19): To a round bottom flask was added alkyne 18 (1.56 g, 8.84 mmol), 2-nitroimidazole 10 (1 g, 8.84 mmol) and K$_2$CO$_3$ (1.22 g, 8.84 mmol) in DMF (10 mL). The reaction was stirred overnight. The reaction was diluted with water (100 mL) and the resultant precipitate (1.2 g) was filtered off and washed with water (2×40 mL). The aqueous layer was extracted into EtOAc. The organic layer was concentrated to dryness and combined with the precipitate. The material was purified on a silica gel cartridge using EtOAc:Hex as the eluent to afford a 19 white solid (324 mg, 18%). Mass Spec (lo-res): Calc'd for C$_8$H$_8$N$_4$O$_3$: 208.06; found: 209.10 (M+H).

N-((1-(2-Hydroxyethyl)-1H-1,2,3-triazol-4-yl)methyl)-2-(2-nitro-1H-imidazol-1-yl)acetamide (20): To a vial was added alkyne (375 mg, 1.8 mmol) and azidoethanol (157 mg, 1.8 mmol). To this vial was added THF (5 mL), DIPEA (345 μL, 1.98 mmol) and copper iodide (34.3 mg, 0.18 mmol). After a few hours, sodium ascorbate (50 mg) was added to force the reaction to completion. The material was then purified on a silica gel column using EtOAc:Hex as the eluent. The material was then further purified via recrystallization using EtOAc:Hex to afford 300 mg (56% yield) of 20 as a solid.

N-((1-(2-Hydroxyethyl)-1H-1,2,3-triazol-4-yl)methyl)-2-(2-nitro-1H-imidazol-1-yl)acetamide (20): To a vial is added alkyne (375 mg, 1.8 mmol) and azidoethanol (157 mg, 1.8 mmol). The solution is heated at 60° C. overnight. The material is then purified on a silica gel column using EtOAc:Hex as the eluent. The material is then further purified via recrystallization using EtOAc:Hex to afford 20 as a solid.

2-(4-((2-(2-Nitro-1H-imidazol-1-yl)acetamido)methyl)-1H-1,2,3-triazol-1-yl)ethyl 4-methylbenzenesulfonate (21): To a round bottom flask was added the alcohol 20 (106 mg, 0.359 mmol), TEA (36.3 mg, 0.359 mmol) and DCM (10 mL). Ts₂O (117 mg, 0.359 mmol) was added in one portion. The reaction was stirred at RT for 4 hrs. The reaction was then concentrated to dryness and purified on a silica gel cartridge using EtOAc:Hex as the eluent to afford 55 mg (34% yield) of 21 as a white solid. Mass Spec (lo-res): Calc'd for $C_{17}H_{19}N_7O_6S$: 449.11; found: 450.1 (M+H).

N-((1-(2-Fluoroethyl)-1H-1,2,3-triazol-4-yl)methyl)-2-(2-nitro-1H-imidazol-1-yl)acetamide (5): To a round bottom flask containing alcohol 20 (20 mg, 0.07 mmol) in DCM (5 mL) at 0° C. was added BAST (20.3 mg, 0.126 mmol). The reaction was stirred at 0° C. for 1 hr. The reaction was concentrated in vacuo and purified on a silica gel cartridge using EtOAc:Hex as the eluent to afford 5 as a clear, colorless oil.

Preparation of Compounds 1 and 26:

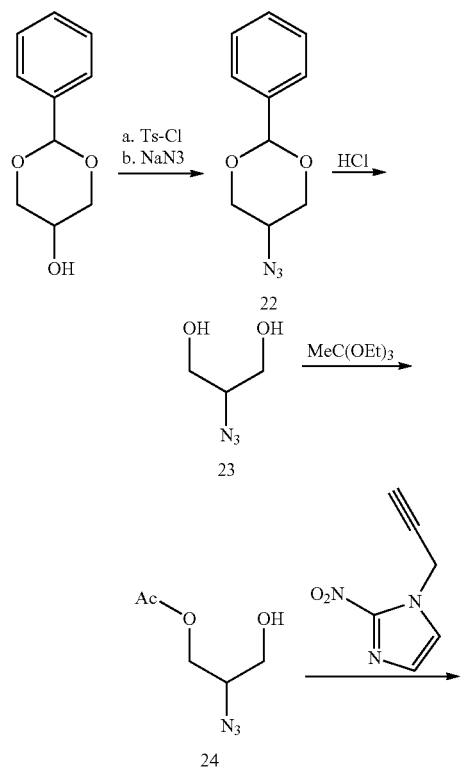

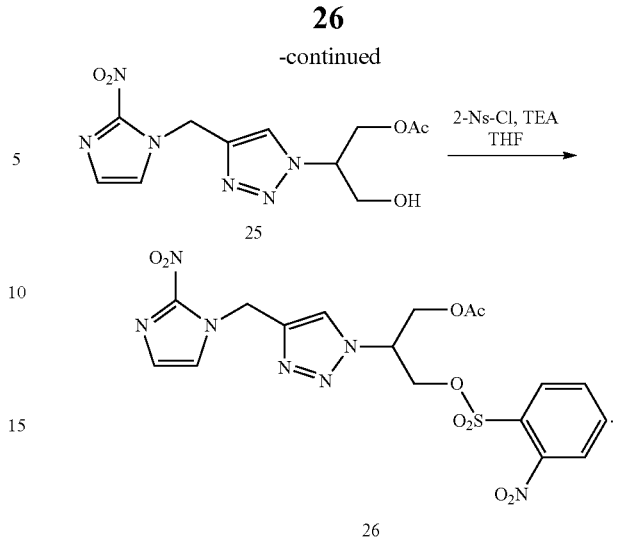

2-Phenyl-1,3-dioxan-5-yl 4-methylbenzenesulfonate: To a 2 liter round bottom flask was added 2-phenyl-1,3-dioxan-5-ol (50 g, 277 mmol), triethyl amine (42.1 g, 416 mmol), DMAP (3.39 g, 27.7 mmol) and dichloromethane (1 L). The reaction was cooled to 0° C. To this solution was added tosyl chloride (58.2 g, 305 mmol) and the reaction was stirred overnight at RT. The reaction was poured onto water (800 mL) and extracted into DCM. The organic layers were combined and concentrated to dryness. The crude mixture was recrystallized from EtOAc:Hex to afford 88 g (96% yield) of a white solid. ¹H NMR (CDCl₃, 400 MHz), δ: 2.44 (3H, s), 4.09 (2H, dd, J=13.6, 2 Hz), 4.27 (2H, dd, J=13.6, 1.6 Hz), 4.51 (2H, pseudo t, J=1.6 Hz), 7.33-7.36 (5H, m), 7.44-7.45 (2H, m), 7.85 (2H, d, J=8.39 Hz). Mass Spec (lo-res): Calc'd for $C_{17}H_{18}O_5S$: 334.09; found: 335.1 (M+H).

5-Azido-2-phenyl-1,3-dioxane (22): To a 1 L round bottom flask was added 2-phenyl-1,3-dioxan-5-yl 4-methylbenzenesulfonate (40 g, 120 mmol) and DMF (500 mL). NaN₃ (31.3 g, 478 mmol) was added as a solution in water (150 mL). The reaction was stirred at 105° C. for 2 days. The reaction was then concentrated to dryness. The solid was dissolved in water (700 mL) and extracted into EtOAc (3×500 mL). The combined organic layers were washed with water (5×) and concentrated to dryness to afford an orange solid. The material was then recrystallized from hexanes to afford 20.7 g (84% yield) of 22 as a pale brown solid. ¹H NMR (CDCl₃, 400 MHz), δ: 3.67 (2H, pseudo t, J=11.59 Hz), 3.78-3.88 (1H, m), 4.36-4.04 (2H, m), 7.36-7.39 (3H, m), 7.45-7.47 (2H, m). Mass Spec (lo-res): Calc'd for $C_{10}H_{11}N_3O_2$: 205.09; found: 178.1 (M+H-N₂).

2-Azidopropane-1,3-diol (23): To a 1 L round bottom flask containing 22 (21.7 g, 106 mmol) in Et₂O (294 mL) was conc. HCl (126 mL). The reaction was stirred at RT overnight. The material was then concentrated in vacuo over silica gel and purified using EtOAc:Hex as the eluent (20% EtOAc to 100% EtOAc) to afford 10.5 g (84% yield) of 23 as a yellow/amber oil. ¹H NMR (CDCl₃, 400 MHz), δ: 1.94 (2H, br s), 3.63-3.68 (1H, m), 3.75-3.86 (4H, m).

2-Azido-3-hydroxypropyl acetate (24): 2-Azidopropane-1,3-diol 23 (10.46 g, 89.3 mmol) was dissolved in CH₂Cl₂ (450 mL) and treated with a catalytic amount of p-toluene sulfonic acid monohydrate (340 mg, 1.8 mmol) and triethylorthoacetate (24.4 mL, 134 mmol) at room temperature for 1 hr. After the formation of the orthoester was complete, a stoichiometric amount of water (2.4 mL, 134 mmol) was added to the mixture. The mixture was then stirred for 40 min and then concentrated in vacuo. Purification of the residue on a silica gel cartridge using EtOAc:Hex as the eluent (5% EtOAc to 100% EtOAc) afforded 8.14 g (57% yield) of 24 as a clear, colorless oil. $^1$H NMR (CDCl$_3$, 400 MHz), δ: 2.45 (1H, br s), 2.12 (3H, s), 3.63-3.78 (3H, 4.20-4.30 (2H, m).

3-Hydroxy-2-(4-((2-nitro-1H-imidazol-1-yl)methyl)-1H-1,2,3-triazol-1-yl)propyl acetate (25): A vial containing Compound 24 (500 mg, 3.14 mmol) and 1-propynyl-2-nitroimidazole (475 mg, 3.14 mmol) was heated at 60° C. overnight. The resultant solid was purified on a silica gel cartridge using EtOAc:Hex as the eluent to afford 504 mg (52% yield) of a white solid.

3-Hydroxy-2-(4-((2-nitro-1H-imidazol-1-yl)methyl)-1H-1,2,3-triazol-1-yl)propyl acetate (25): A vial containing Compound 24 (5.5 g, 34.9 mmol) in t-BuOH:THF:H$_2$O (120 mL, 1:1:1) was added CuSO$_4$.5H$_2$O (435 mg, 1.75 mmol), sodium ascorbate (691 mg, 3.49 mmol) and 1-propynyl-2-nitroimidazole (5.27 g, 34.9 mmol) and the reaction was stirred overnight at room temperature. The reaction was then concentrated to dryness over silica. The resultant solid was purified on a silica gel cartridge using 50% EtOAc:Hex followed by 10% MeOH:DCM as the eluent to afford 9.17 g (90% yield) of a viscous yellow oil. $^1$H NMR (CDCl$_3$, 400 MHz), δ: 2.06 (3H, s), 4.11-4.13 (2H, m), 4.47-4.59 (2H, m), 4.81-4.84 (1H, m), 5.72 (2H, s), 7.17 (1H, d, J=1.12 Hz), 7.38 (1H, d, J=1.12 Hz), 7.88 (1H, s). Mass Spec (lo-res): Calc'd for C$_{11}$H$_{14}$N$_6$O$_5$: 310.10; found: 311.10 (M+H).

(2-(4-((2-Nitro-1H-imidazol-1-yl)methyl)-1H-1,2,3-triazol-1-yl)-3-(2-nitrophenylsulfonyloxy)propyl acetate) 26: To a round bottom flask containing 25 (9.17 g, 29.6 mmol) in DCM (200 mL) at 0° C. was added TEA (8.3 mL, 59.2 mmol) and 4 Å molecular sieves (2 g). The reaction was stirred for 1 hr. 2-nitrobenzenesulfonyl chloride (7.87 g, 35.5 mmol) was added and the reaction was allowed to warm to RT. The reaction was stirred at RT for 2 hrs. The reaction was concentrated in vacuo onto silica gel and purified on a silica gel cartridge using MeOH:DCM (2% MeOH:DCM to 10% MeOH:DCM) as the eluent to afford 9.74 g of a pale yellow solid. The material was further purified via recrystallization using EtOAc:Hex to afford 4.5 g (30.5% yield) of a white solid. $^1$H NMR (CDCl$_3$, 400 MHz), δ: 2.06 (3H, s), 4.54 (2H, d, J=5.6 Hz), 4.75 (2H, dt, J=11.2, 6.80), 5.12-5.16 (1H, m), 5.68 (2H, d, J=3.20), 7.17 (1H, d, J=0.8 Hz), 7.33 (1H, d, J=1.12 Hz), 7.75-7.87 (4H, m), 8.09 (1H, dd, J=7.59, 1.2 Hz). Mass Spec (lo-res): Calc'd for C$_{17}$H$_{17}$N$_7$O$_9$S: 495.08; found: 496.10 (M+H).

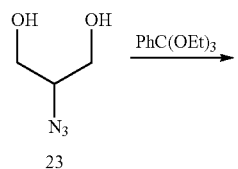

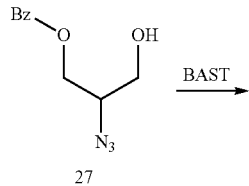

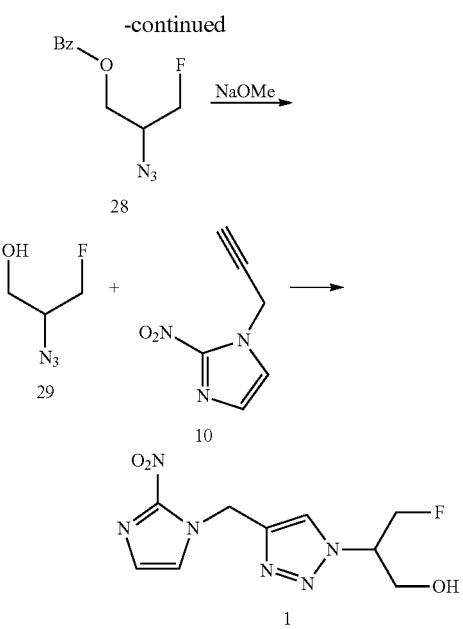

2-Azido-3-hydroxypropyl benzoate (27): Neat 23 (1.48 g, 12.65 mmol) was dissolved in CH$_2$Cl$_2$ (127 mL) and treated with a catalytic amount of p-toluene sulfonic acid monohydrate (0.048 g, 20 μmol) and (trimethoxymethyl)benzene (3.26 mL, 18.98 mmol) in CH$_2$Cl$_2$ at room temperature for 1 hr. After the formation of the orthoester was complete, a stoichiometric amount of water (340 μL, 18.98 mmol) was added to the mixture. The mixture was then stirred for 40 min and concentrated in vacuo. Purification of the residue by silica gel flash chromatography using 25% EtOAc/hexanes gave 2.6 g of monoacylated product 27 (93% yield) as a clear, colorless oil. $^1$H NMR (CDCl$_3$, 400 MHz) δ: 8.03-8.06 (m, 2H), 7.58 (tt, J=1.6, 2.0, 1.6 1H), 7.43-7.47 (m, 2H), 4.54 (dd, J=4.4, 12.0 Hz, 1H), 4.46 (dd, J=6.8, 12.0 Hz, 1H), 3.85-3.91 (m, 1H), 3.80 (dd, J=4.8, 11.6 Hz, 1H), 3.73 (dd, J=6.0, 11.6 Hz, 1H).

2-Azido-3-fluoropropyl benzoate (28): Compound 27 (9 g, 40.72 mmol) was dissolved in CH$_2$Cl$_2$ (70 mL) and treated dropwise at room temperature with BAST (3.75 mL, 20.36 mmol). After stirring for 1 hr, an additional 3.75 mL (20.36 mmol) of BAST was added dropwise at room temperature. After stirring for a further 1 hr, an additional 3.75 mL (20.36 mmol) of BAST was added dropwise at room temperature and the reaction mixture was stirred for 12 hr. The reaction mixture was quenched with saturated NaHCO$_3$, the organic layer was consecutively washed with H$_2$O and brine and dried over MgSO$_4$, and the solvent removed under vacuum. The residue was purified on silica gel using 25% Ether:hexanes as the eluent to afford 3.24 g (37% yield) of 28 as a clear, colorless oil. 5 g of 27 was also recovered. $^1$H NMR (CDCl$_3$, 400 MHz) δ: 8.04-8.07 (m, 2H), 7.60 (tt, J=1.6, 2.0, 1.6 1H), 7.45-7.49 (m, 2H), 4.62-4.70 (m, 1H), 4.52-4.57 (m, 2H), 4.42-4.46 (m, 1H), 3.98-4.08 (m, 1H), 3.73 (dd, J=6.0, 11.6 Hz, 1H).

2-Azido-3-fluoropropan-1-ol (29): Compound 28 (1.63 g, 7.30 mmol) was dissolved in methanol (15 mL) and treated with NaOMe (0.8 g, 14.8 mmol) at room temperature. After stirring for 1 hr, silica was added to the reaction mixture and the solvent was evaporated and purified on silica gel using 50% EtOAc/hexanes as the eluent to afford 0.828 g of 29

(95% yield) as a clear, colorless oil. $^1$H NMR (CDCl$_3$, 400 MHz) δ: 4.59-4.68 (m, 1H), 4.47-4.56 (m, 1H), 3.68-3.84 (m, 3H).

3-Fluoro-2-(4-((2-nitro-1H-imidazol-1-yl)methyl)-1H-1,2,3-triazol-1-yl)propan-1-ol (1): To a vial is added alkyne 10 (1.9 g, 12.6 mmol) and 29 (1.5 g, 12.6 mmol). The solution is heated at 60° C. overnight. The material is then purified on a silica gel column using 10% MeOH:CH$_2$Cl$_2$ as the eluent. The material is then further purified via recrystallization using EtOAc:Hex to afford 1 as a solid.

3-Fluoro-2-(4-((2-nitro-1H-imidazol-1-yl)methyl)-1H-1,2,3-triazol-1-yl)propan-1-ol (1): A solution of 10 (1.9 g, 12.6 mmol) and 29 (1.5 g, 12.6 mmol) in t-BuOH:THF:H$_2$O (22.5 mL, 1:1:1) was treated with CuSO$_4$.5H$_2$O (0.31 g, 1.26 mmol) and sodium ascorbate (0.5 g, 2.52 mmol) and stirred for 1 hr at room temperature. Organic solvents removed under vacuum, the residue dissolved in CH$_2$Cl$_2$ and consecutively washed with H$_2$O, then brine, then dried over MgSO$_4$. The solvent was then concentrated in vacuo and the residue was purified on silica gel using 10% MeOH:CH$_2$Cl$_2$ as the solvent to afford 1 (3.00 g, 88%) as white solid. The product was further purified via recrystallization from EtOAc/hexanes. $^1$H NMR ((CD$_3$)$_2$CO, 400 MHz) δ: 8.15 (s, 1H), 7.57 (d, J=1.2 Hz, 1H), 7.11 (d, J=1.2 Hz, 1H), 5.79 (s, 2H), 4.87-5.05 (m, 2H), 4.82 (dd, J=4.0, 10.0 Hz, 1H), 4.17-4.45 (m, 1H), 4.03 (t, J=5.6 Hz, 2H). $^{13}$C NMR ((CD$_3$)$_2$CO, 100 MHz) δ: 141.8, 127.9, 127.1, 123.5, 83.0, 81.3, 63.0 (d, J=18.69 Hz, 1C), 60.5 (d, 6.73 Hz, 1C), δ: 44.8; $^{19}$F NMR ((CD$_3$)$_2$CO, 376 MHz) 230.2 (ddd, J=19.18, 19.55, 21.60 Hz, 1F); Mass Spec (lores): Calc'd for C$_9$H$_{11}$FN$_6$O$_3$: 270.09; found: 271.1 (M+H).

Description of the Radiolabeling Process for [F-18]-Labeled Hypoxia Tracers: General Preparation for Preparing [F-18]Fluoride for Radiolabeling:

The reaction takes place in an Explora® RN chemistry module, which is controlled by a computer using the GINA-Star software.

[F-18]Fluoride ion preparation: Aqueous [F-18]fluoride ion, which is produced in the cyclotron target, is delivered to and then trapped on an anion exchange resin cartridge located on the chemistry module. The F-18 is then eluted into the reaction vessel using a solution of potassium carbonate (3 mg) in water (0.4 mL). Kryptofix® 222 (20 mg) dissolved in acetonitrile (1 mL) is then added to the reaction vessel.

The solution is concentrated to dryness to remove the acetonitrile and water (70-95° C., under reduced pressure (250 mbar) and a stream of argon), which will afford a relatively dry, highly activated form of [F-18]fluoride ion.

Radiolabeling Reaction for [F-18]8:

A solution of the precursor 12, (20 μmol) in acetonitrile (0.9 mL) is added to the dried [F-18]fluoride ion. The mixture is heated to approximately 110° C. for 10 minutes to allow reaction with the [F-18]fluoride ion.

Purification of reaction mixture and sterile filtration: The crude [F-18]-labeled tracer product solution is transferred to the sample loop (1.5 mL) and then injected onto the semi-preparative HPLC column (Ex. ACE C18, 5AQ, 250×10 mm, 10% ethanol/10% water (v/v), 4.0 mL/min).

The Explora® RN chemistry module is equipped with both UV and Geiger Mueller (GM) detectors. The product is collected from the column as monitored by flow-through radioactivity and UV (254 nm) detectors.

Under the described elution conditions, the retention time of the [F-18]8 is approximately 8-10 minutes. The fraction containing the [F-18]-labeled tracer is passed through a sterile filter (0.22 μm) and collected into a sterile vial. The volume of the drug substance collected is typically 8-10 mL.

Radiolabeling Reaction for [F-18]8

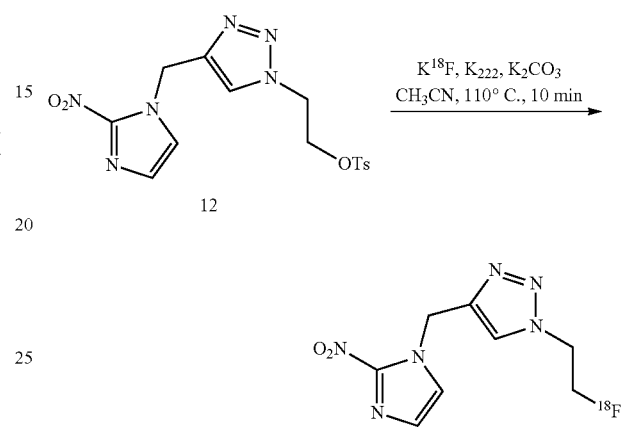

Radiochemical yield: 2.05% decay corrected

Radiochemical purity: 100%

Radiolabeling Reaction for [F-18]3:

A solution of the precursor 16, (15±5 mg, 20-40 μmol) dissolved in a mixture of acetonitrile (0.5 mL) and t-BuOH (0.5 mL) is added to the reaction vessel containing the anhydrous [F-18]Fluoride. The vessel is heated to 125±15° C. for 7.5±2.5 minutes to induce displacement of the nosylate leaving group by [F-18]fluoride.

After cooling and evaporating the acetonitrile and t-butanol, aqueous hydrochloric acid (1.0 N, 0.8 mL) is added and the mixture heated to 110±5° C. for 7.5±2.5 minutes. This hydrolyzes the acetate group converting it to a hydroxyl group. This hydrolysis reaction results in the formation of crude [F-18]3. The reaction mixture is cooled and neutralized by addition of sodium acetate (2.0 M, 0.4 mL).

Purification of reaction mixture and sterile filtration: The crude [F-18]-labeled tracer product solution is transferred to the sample loop (1.5 mL) and then injected onto the semi-preparative HPLC column (Ex. Synergi, 250×10 mm, 5% ethanol/95% water (v/v), 5.0 mL/min).

The Explora® RN chemistry module is equipped with both UV and Geiger Mueller (GM) detectors. The product is collected from the column as monitored by flow-through radioactivity and UV (254 nm) detectors.

Under the described elution conditions, the retention time of the [F-18]3 is approximately 8-10 minutes. The fraction containing the [F-18]-labeled tracer is passed through a sterile filter (0.22 μm) and collected into a sterile vial. The volume of the drug substance collected is typically 8-10 mL.

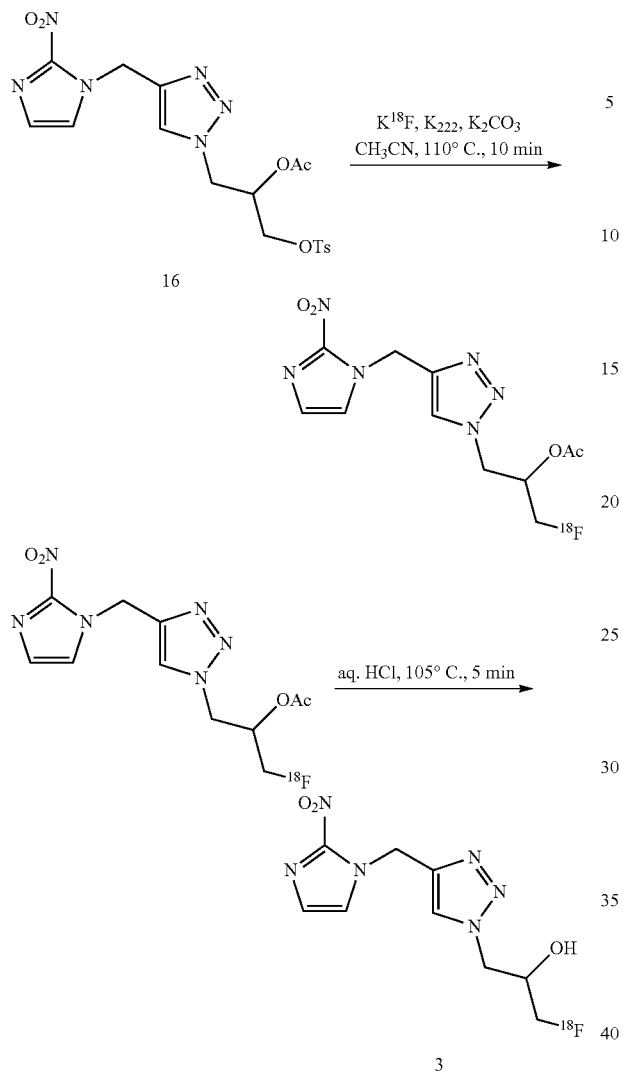

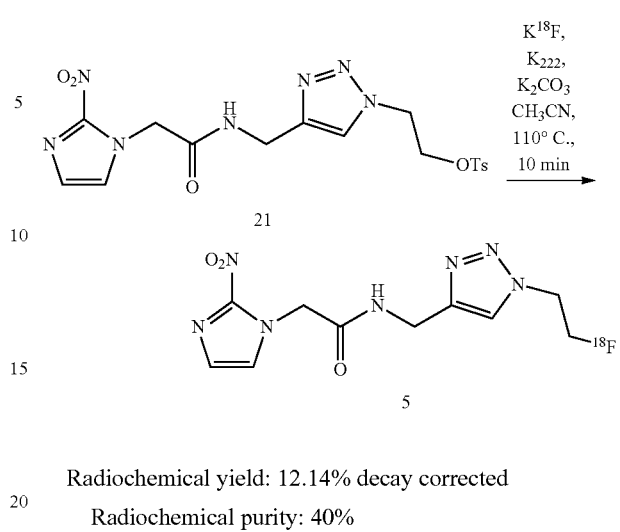

Radiochemical yield: 12.14% decay corrected

Radiochemical purity: 40%

Radiolabeling Reaction for [F-18]1:

A solution of the precursor 26, (15±5 mg, 20-40 μmol) dissolved in a mixture of acetonitrile (0.5 mL) and t-BuOH (0.5 mL) is added to the reaction vessel containing the anhydrous [F-18]Fluoride. The vessel is heated to 125±15° C. for 7.5±2.5 minutes to induce displacement of the nosylate leaving group by [F-18]fluoride.

After cooling and evaporating the acetonitrile and t-butanol, aqueous hydrochloric acid (1.0 N, 0.8 mL) is added and the mixture heated to 110±5° C. for 7.5±2.5 minutes. This hydrolyzes the acetate group converting it to a hydroxyl group. This hydrolysis reaction results in the formation of crude [F-18]1. The reaction mixture is cooled and neutralized by addition of sodium acetate (2.0 M, 0.4 mL).

Purification of reaction mixture and sterile, filtration: The reaction mixture containing crude [F-18]1 is passed through a alumina sep-pak lite (to remove unreacted [F-18]fluoride) and then transferred to the HPLC sample loop. The crude reaction material was purified via chromatographic separation using a semi-preparative HPLC column (Waters ACE AQ reverse phase semi-prep column (250×10 mm), p/n ACE-126-2510, 250×10 mm, 5% ethanol in 21 mM 95% Phosphate Buffer, 5.0 mL/min). The column effluent is monitored using UV (254 nm) and radiometric detectors connected in series.

The Explora® RN chemistry module is equipped with both UV and Geiger Mueller (GM) detectors. The product is collected from the column as monitored by flow-through radioactivity and UV (254 nm) detectors. Under the described elution conditions, the retention time of the [F-18]1 is approximately 17±5 minutes. A sterile empty collection vial is preloaded with 5-10 mL of sterile diluent containing 1-6% ethanol, 75 mg/mL of ascorbic acid and 95% 21 mM phosphate. The purified [F-18]1 fraction eluted from the HPLC purification column is processed through a 0.2 μm sterile filter into the preloaded collection vial. Based on an in-process assay for total radioactivity, sufficient ascorbic acid and sterile diluent is added to adjust the ascorbic acid concentration to 5% (50 mg/mL) and the radioactive concentration to not more than 30 mCi/mL.

Radiochemical yield: 38.42% decay corrected

Radiochemical purity: 100%

Radiolabeling Reaction for [F-18]5:

A solution of the precursor 21, (15±5 mg, 20-40 μmol) dissolved in a mixture of acetonitrile (0.5 mL) and t-BuOH (0.5 mL) is added to the reaction vessel containing the anhydrous [F-18]Fluoride. The vessel is heated to 125±15° C. for 7.5±2.5 minutes to induce displacement of the nosylate leaving group by [F-18]fluoride.

Purification of reaction mixture and sterile filtration: The crude [F-18]-labeled tracer product solution is transferred to the sample loop (1.5 mL) and then injected onto the semi-preparative HPLC column (Ex. Synergi, 250×10 mm, 8% ethanol in 21 mM: 92% Phosphate Buffer (v/v), 4 ml/min).

The Explora® RN chemistry module is equipped with both UV and Geiger Mueller (GM) detectors. The product is collected from the column as monitored by flow-through radioactivity and UV (254 nm) detectors.

Under the described elution conditions, the retention time of the [F-18]5 is approximately 7-9 minutes. The fraction containing the [F-18]-labeled tracer is passed through a sterile filter (0.22 μm) and collected into a sterile vial. The volume of the drug substance collected is typically 8-10 mL.

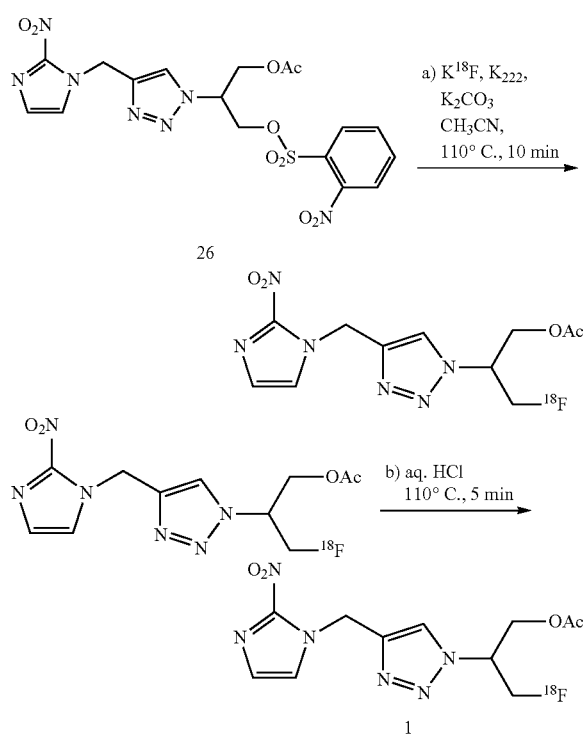

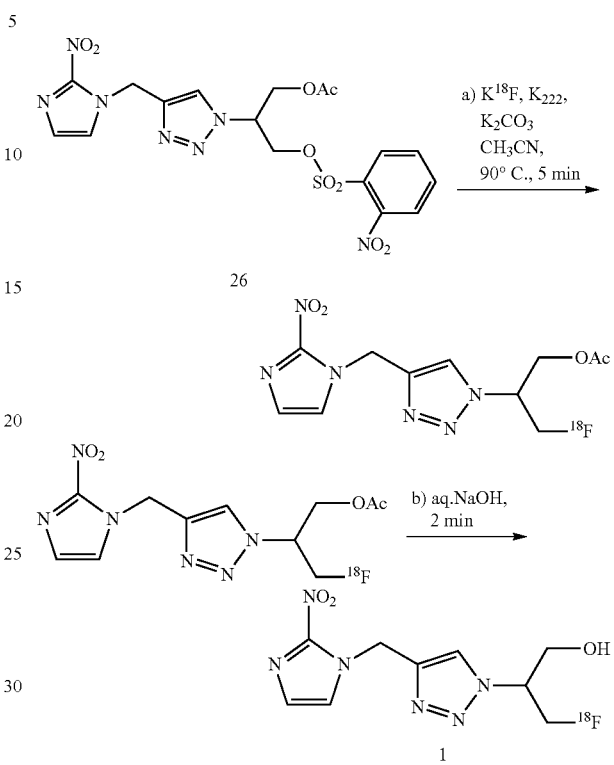

Radiochemical yield: 34% decay corrected
Radiochemical purity: 100%
Alternate Radiolabeling Reaction for [F-18]1:

Radioactive [F-18]fluoride is transferred into a 3 mL V-vial with 0.5 mL of K222/$K_2CO_3$ solution (660 mg of K222 and 210 mg of $K_2CO_3$ in 9 mL of MeCN and 9 mL of $H_2O$). The [F-18]Fluoride is azeotropically dried with 3×1 mL MeCN under Ar flow. A solution of the precursor 26, (16±5 mg, 20-40 µmol) dissolved in acetonitrile (1.0 mL) is added to the reaction vessel containing the anhydrous [F-18]Fluoride. The vessel is heated to 95±5° C. for 7.5±2.5 minutes to induce displacement of the nosylate leaving group by [F-18]fluoride.

After cooling and evaporating the acetonitrile to approximately 0.1 mL, aqueous NaOH (0.05 N, 2.0 mL) is added and the mixture heated to 60±5° C. for 3±1 minutes. This hydrolyzes the acetate group converting it to a hydroxyl group. This hydrolysis reaction results in the formation of crude [F-18]1.

Purification of reaction mixture and sterile filtration: The crude reaction material was purified via chromatographic separation using a semi-preparative HPLC column (Phenomenex Luna reverse phase semi-prep column (250×10 mm, 10µ), 6% ethanol, 5.0 mL/min). The column effluent is monitored using UV (254 nm) and radiometric detectors connected in series.

The Explora® RN chemistry module is equipped with both UV and Geiger Mueller (GM) detectors. The product is collected from the column as monitored by flow-through radioactivity and UV (254 nm) detectors. Under the described elution conditions, the retention time of the [F-18]1 is approximately 17±5 minutes. A sterile empty collection vial is preloaded with 5-10 mL of sterile diluent containing 1-6% ethanol, 75 mg/mL of ascorbic acid and 95% 21 mM phosphate. The purified [F-18]1 fraction eluted from the HPLC purification column is processed through a 0.2 µm sterile filter into the preloaded collection vial. Based on an in-process assay for total radioactivity, sufficient ascorbic acid and sterile diluent is added to adjust the ascorbic acid concentration to 5% (50 mg/mL) and the radioactive concentration to not more than 30 mCi/mL.

Radiochemical yield: 34% decay corrected
Radiochemical purity: 100%
Biological Data for HX Series
Animal Experiments
1) Bio-Distribution and Bio-Stability of HX4
1A: Study in Mice Method: Compound 1 was dissolved in DMSO to achieve a 100 mM stock solution. This was then diluted with 1× PBS containing 3% Solutol to achieve a concentration of 5 mM. 200 µl of 5 mM Compound 1 solution was injected into the tail vein in mice animals under isofluorane anesthesia. The in vivo uptake was two hours.

Blood and urine samples were collected at 30, 60, 90 and 120 minutes. Samples were immediately placed on ice to prevent compound degradation. After blood and urine sampling were completed at 120 minutes, the mouse was sacrificed by cervical dislocation. The following whole organs were harvested within 30-40 minutes in the following order; lower GI, upper GI, spleen, pancreas, gall bladder, liver, heart, kidneys, lungs, about 0.3 gram of muscle from both legs, about 0.4 gram of skin at the back, the entire brain and about 0.4 gram of fat inside the abdomen.

To the samples were added a proportional amount of lysis buffer (about 5 ml/gram tissue) before the tissue was homogenized using a powered homogenizer, 50 µL of lysis buffer was added to the blood and urine samples, followed by briefly vortexing. 200 µl of organ homogenate was sampled into a 1.5 ml Eppendorf tube. All samples were heated at 100° C. for 2 minutes to denature the proteins and then placed in ice for 15 minutes. Then 40 µl of formic acid was added to the organ samples and 20 µl was added to the blood and urine samples. All tubes were vortexed to achieve complete mixing of sample with acid. Samples were then placed on ice for 15 minutes before being centrifuged at 13000 rpm for 15 minutes at 4° C. 30 µl of the supernatant was transferred to an HPLC vial for MSD analysis.

A standard curve with a wide range of Compound 1 concentrations was prepared using the same method described above for tissue lysate treatment. The corresponding peak of the compound was identified first in the standards. The areas of the peaks were measured and converted into a standard correlation curve for estimation of Compound 1 concentration in the samples. The amount of compound in each sample is expressed as % injected dose/gram tissue (% ID/g tissue).

1B: Study in Rats

Method: Compound 1 solution was prepared as described previously. One ml of 10 mM Compound 1 solution was injected intravenously (tail vein) into rats under isofluorane anesthesia. Blood and urine samples were collected before injection and at 15, 30, 60, 90 and 120 minutes after injection. Samples treatments and LC/MS measurement are the same as the mouse samples described in 1A.

Results:

Mouse Data (FIG. 1):

In mouse, the blood level of Compound 1 was 4.1% ID/g at 30 minutes and decreased to 0.59% at 120 minutes. Blood clearance and urine excretion is fast given the high % ID/g in urine and low % ID/g in blood (95.6% ID/g at 30 minute urine, 4.1% ID/g at 30 minute blood). The urine excretion index (averaged urine % ID/g divided by blood % ID/g at 120 minute) was 88.69. The levels of Compound 1 in gall bladder and GI system are low.

Rat Data (FIG. 2):

In rats, the blood levels of Compound 1 are 0.67 and 0.15% ID/g at 30 and 120 minutes, respectively. The urine level was 5.3% ID/g at 30 minute. The urine excretion index (averaged urine % ID/g divided by blood % ID/g at 120 minute) was 36.62. Thus, Compound 1 in rat urine excretion and blood clearance is fast given the high % ID/g in the urine and low % ID/g in the blood.

2) Cytotoxicity Assays of HX4 in Human Normal and Cancer Cell Lines

Method: The assay is based on the ability of viable cells to reduce 3-[4,5-dimethylthiazol-2-yl]-2,5-diphenyl tetrazolium bromide to colored formazan crystals. Ls174T human colorectal adenocarcinoma, A172 human brain glioblastoma, MRC5 human normal lung fibroblast, and ALM12 mouse normal liver cell lines were selected for this study. Cells were cultured with different concentration of Compound 1 (0, 100, 500, 1000, 5000, 10000 nM) for 24 hours and then incubated with 0.5 mg/ml of 3-[4,5-dimethylthiazol-2-yl]-2,5-diphenyl tetrazolium bromide for 1 hour. Cells were lysed and formazan crystals were dissolved with 2-propanol for 1 hour and the optical density of the resultant colored 2-propanol was measured. The percentages of cell survival were calculated based on the optical densities.

Results: In all of these four cell lines (normal and cancerous), statistically, the numbers of viable cells treated with different concentrations of Compound 1 showed no difference from those of untreated control cells. Thus, Compound 1 is not cytotoxic to normal or cancer cells (FIGS. 3-5).

Imaging Protocol: (FIG. 6)

Animals were anesthetized using isoflurane/oxygen inhalation for the duration of each PET scanning procedure (up to 2 hours). Anesthetized animals were placed on a heated pad for the duration of each PET scan. Typical injection volumes were 250 µL typically containing 250 µCi of activity. Continuous, dynamic PET scanning commenced immediately following administration of the F18-labeled tracer.

It will be appreciated by those skilled in the art that changes could be made to the embodiments described above without departing from the broad inventive concept thereof. It is understood, therefore that this invention is not limited to the particular embodiments disclosed, but it is intended to cover modifications that are within the spirit and scope of the invention, as defined by the appended claims. While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

What is claimed:

1. A compound consisting of formula I:

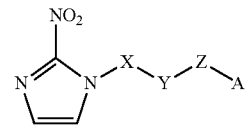

or a pharmaceutically acceptable salt thereof, optionally in the form of a single stereoisomer or mixtures of stereoisomers thereof, wherein:

X is a $(C_1-C_{10})$alkylenyl, wherein at least one of the $(C_1-C_{10})$alkylenyl carbon atoms is optionally replaced by —CO—, —CONR'—, —NR'CO—, —NR'—, —O—, —S—, a $(C_3-C_8)$cycloalkyl or a $(C_3-C_8)$heterocycloalkyl ring, wherein at least one of the atoms of the $(C_3-C_8)$cycloalkyl or a $(C_3-C_8)$heterocycloalkyl ring is unsubstituted or substituted with 1, 2, 3 or 4 $X^1$, or a combination thereof;

each $X^1$ is independently selected from the group consisting of hydroxyl, thiol, amino, alkyl, alkoxy, thioalkyl and halo;

Y is a triazolyl of the formula:

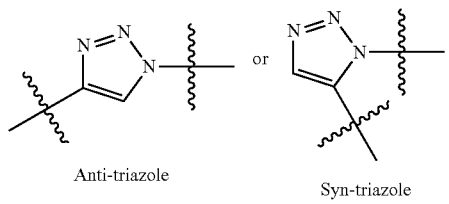

Anti-triazole    Syn-triazole

Z is a $(C_1-C_{10})$alkylenyl group wherein at least one of the atoms of the $(C_1-C_{10})$alkylenyl group is optionally replaced by —CO—, —CONR"—, —NR"CO—, —NR"—, —O— and —S—, and wherein at least one of the atoms of the $(C_1-C_{10})$alkylenyl group is unsubstituted or substituted with 1, 2, 3 or 4 $X^1$;

A is a radioactive isotope; and

R' and R" are each independently H or are each independently selected from the group consisting of $(C_1-C_6)$alkyl, —CO$(C_1-C_3)$alkyl, —CONH$(C_1-C_3)$alkyl and —CO$_2(C_1-C_3)$alkyl.

2. The compound of claim 1, wherein X is a (C$_1$-C$_4$)alkylenyl group and wherein at least one atom is optionally substituted with 1, 2 or 3 hydroxyl groups or 1, 2 or 3 —NH$_2$ or —NH(C$_1$-C$_4$)alkyl groups.

3. The compound of claim 2, wherein X is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH$_2$—CH(OH)—CH$_2$—, —CH$_2$—CH$_2$—CH(OH)— and —CH$_2$—CH(OH)—CH(OH)—CH$_2$—.

4. The compound of claim 1, wherein X is selected from the group consisting of —CONR'—, —(C$_1$-C$_4$)alkylCONR'—, —CONR'(C$_1$-C$_4$)alkyl- and —(C$_1$-C$_4$)alkylCONR'(C$_1$-C$_4$)alkyl, wherein R' is H or (C$_1$-C$_3$)alkyl.

5. The compound of claim 1, wherein A is $^{11}$C, $^{11}$C-Me or $^{18}$F.

6. The compound of claim 1 consisting of formula IIb:

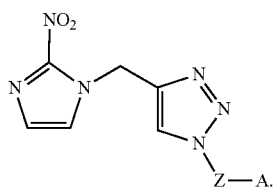

IIb

7. The compound of claim 6, wherein Z is an (C$_1$-C$_4$) alkylenyl group and wherein X$^1$ further consists of (C$_1$-C$_4$) alkyl, (C$_1$-C$_4$)alkoxy and thio(C$_1$-C$_4$)alkyl.

8. The compound of claim 7, wherein Z is selected from the group consisting of —CH$_2$—, —CH$_2$—CH$_2$—, —CH$_2$—CH$_2$—CH$_2$—, —CH$_2$—CH$_2$—CH$_2$—CH$_2$—, —CH$_2$—CH(OH)—, —CH(OH)—CH$_2$—, —CH(OH)—CH$_2$—CH$_2$—, —CH(CH$_2$OH)—CH$_2$—, —CH$_2$—CH(OH)—CH$_2$—, —CH$_2$—CH$_2$—CH(OH)— and —CH$_2$—CH(OH)—CH(OH)—CH$_2$—.

9. The compound of claim 1 consisting of the formula:

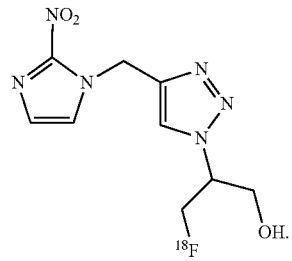

10. The compound of claim 1 consisting of formula IV:

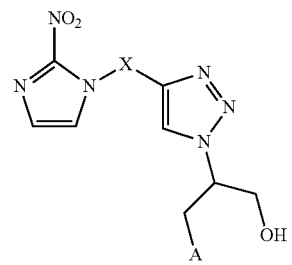

each X$^1$ is independently selected from the group consisting of hydroxyl, thiol, amino, (C$_1$-C$_4$)alkyl, (C$_1$-C$_4$) alkoxy, thio(C$_1$-C$_4$)alkyl and halo; and
A is $^{18}$F, $^{11}$C or $^{11}$CH$_3$O.

11. The compound of claim 1, wherein X is (C$_1$-C$_{10}$)alkylenyl, wherein at least one of the (C$_1$-C$_{10}$)alkylenyl carbon atoms is optionally replaced by a group selected from —CONR'— or —NR'CO—, or wherein 2, 3 or 4 contiguous atoms of the (C$_1$-C$_{10}$)alkylenyl group form a (C$_3$-C$_8$)cycloalkyl, wherein at least one atom of the (C$_3$-C$_8$)cycloalkyl is unsubstituted or substituted with 1, 2 or 3 X$^1$, wherein X$^1$ is —OH or NH$_2$.

12. The compound of claim 1 selected from the group consisting of:

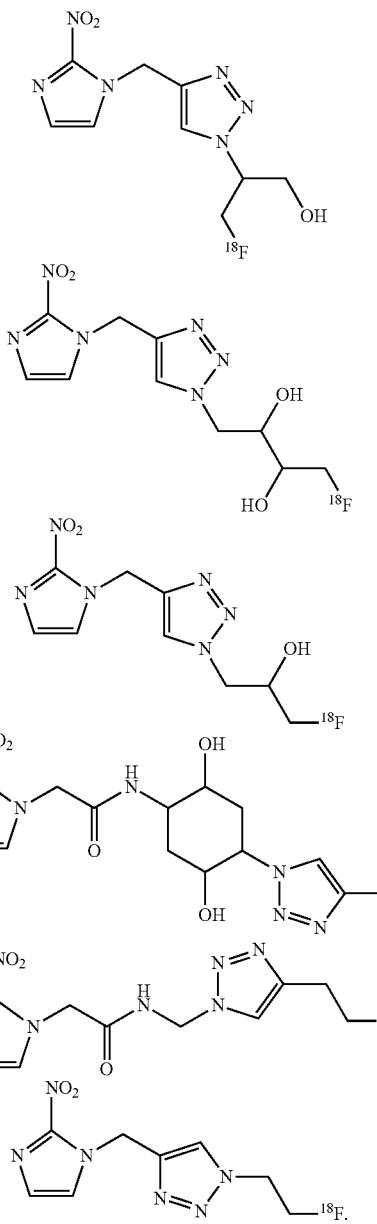

13. The compound of claim 1, wherein Z is a (C$_1$-C$_4$) alkylenyl group and wherein X$^1$ further consists of (C$_1$-C$_4$) alkyl, (C$_1$-C$_4$)alkoxy and thio(C$_1$-C$_4$)alkyl.

14. A pharmaceutical composition comprising a pharmaceutical carrier and a compound comprising formula I:

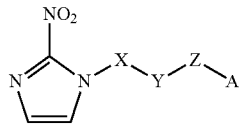

or a pharmaceutically acceptable salt thereof, optionally in the form of a single stereoisomer or mixtures of stereoisomers thereof,
wherein:
X is a $(C_1-C_{10})$alkylenyl, wherein at least one of the $(C_1-C_{10})$alkylenyl carbon atoms is optionally replaced by —CO—, —CONR'—, —NR'CO—, —NR'—, —O—, —S—, a $(C_3-C_8)$cycloalkyl or a $(C_3-C_8)$heterocycloalkyl ring, wherein at least one of the atoms of the $(C_3-C_8)$cycloalkyl or a $(C_3-C_8)$heterocycloalkyl ring is unsubstituted or substituted with 1, 2, 3 or 4 $X^1$, or a combination thereof;
each $X^1$ is independently selected from the group consisting of hydroxyl, thiol, amino, alkyl, alkoxy, thioalkyl and halo;
Y is a triazolyl of the formula;

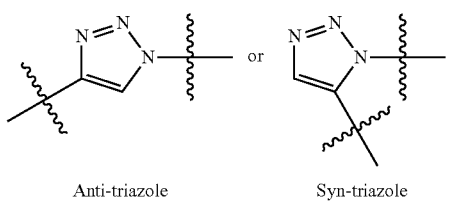

Anti-triazole          Syn-triazole

Z is an $(C_1-C_{10})$alkylenyl group wherein at least one of the atoms of the $(C_1-C_{10})$alkylenyl group is optionally replaced by —CO—, —CONR''—, —NR''CO—, —NR''—, —O— and —S—, and wherein at least one of the atoms of the $(C_1-C_{10})$alkylenyl group is unsubstituted or substituted with 1, 2, 3 or 4 $X^1$;
A is a leaving group, $CH_3$, $CH_3O$, F or $^{18}F$, $^{11}C$, or $^{11}CH_3O$; and
R' and R'' are each independently H or are each independently selected from the group consisting of $(C_1-C_6)$alkyl, —CO$(C_1-C_3)$alkyl, —CONH$(C_1-C_3)$alkyl and —CO$_2(C_1-C_3)$alkyl.

15. A pharmaceutical composition comprising a pharmaceutical carrier and a compound comprising formula I:

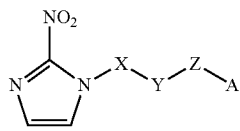

or a pharmaceutically acceptable salt thereof, optionally in the form of a single stereoisomer or mixtures of stereoisomers thereof,
wherein:
X is a $(C_1-C_{10})$alkylenyl, wherein at least one carbon atom is unsubstituted or substituted with 1, 2, 3 or 4 $X^1$;

each $X^1$ is independently selected from the group consisting of hydroxyl, thiol, amino, alkyl, alkoxy, thioalkyl and halo;
Y is a triazolyl of the formula:

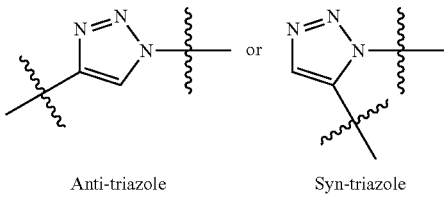

Anti-triazole          Syn-triazole

Z is an $(C_1-C_{10})$alkylenyl group wherein at least one of the carbon atoms of the $(C_1-C_{10})$alkylenyl group is optionally replaced by a group selected from —CO—, —CONR''—, —NR''CO—, —NR''—, —O— and —S—, and wherein at least one atom of the $(C_1-C_{10})$alkylenyl group is unsubstituted or substituted with 1, 2, 3 or 4 $X^1$;
A is a leaving group, $CH_3$, $CH_3O$, halo or a radioactive isotope; and
R'' is H or is selected from the group consisting of $(C_1-C_6)$alkyl, —CO$(C_1-C_3)$alkyl, —CONH$(C_1-C_3)$alkyl and —CO$_2(C_1-C_3)$alkyl.

16. A method for detecting hypoxia in cells, the method comprising:
a) administering to a mammal a compound of formula I:

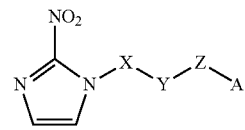

or a pharmaceutically acceptable salt thereof, optionally in the form of a single stereoisomer or mixtures of stereoisomers thereof;
wherein:
X is a $(C_1-C_{10})$alkylenyl, unsubstituted or substituted with 1, 2, 3 or 4 $X^1$, wherein at least one of the $(C_1-C_{10})$alkylenyl carbon atoms is optionally replaced by —CO—, —CONR'—, —NR'CO—, —NR'—, —O— and —S—, a $(C_3-C_8)$cycloalkyl or a $(C_3-C_8)$heterocycloalkyl ring, wherein at least one atom of the $(C_3-C_8)$cycloalkyl or $(C_3-C_8)$heterocycloalkyl ring is unsubstituted or substituted with 1, 2, 3 or 4 $X^1$, or a combination thereof;
each $X^1$ is independently selected from the group consisting of hydroxyl, thiol, amino, alkyl, alkoxy, thioalkyl and halo;
Y is a triazolyl of the formula:

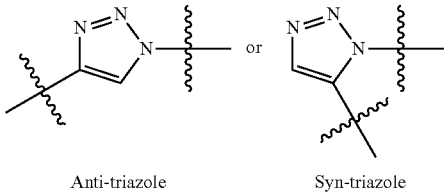

Anti-triazole          Syn-triazole

Z is an ($C_1$-$C_{10}$)alkylenyl group wherein at least one of the carbon atoms of the ($C_1$-$C_{10}$)alkylenyl group is optionally replaced by —CO—, —CONR'—, —NR'CO—, —NR'—, —O— and —S—, and wherein at least one atom of the ($C_1$-$C_{10}$)alkylenyl group is unsubstituted or substituted with 1, 2, 3 or 4 $X^1$;

A is a radioactive isotope; and

R' and R" are each independently H or are each independently selected from the group consisting of ($C_1$-$C_6$) alkyl, —CO($C_1$-$C_3$)alkyl, —CONH($C_1$-$C_3$)alkyl and —$CO_2$($C_1$-$C_3$)alkyl; and b) detecting, by PET, the presence of retained radioactive element in hypoxic cells of the mammal.

17. The method of claim 16, wherein X is a ($C_1$-$C_4$)alkylenyl group and wherein at least one atom is optionally substituted with 1, 2 or 3 hydroxyl groups or 1, 2 or 3 —$NH_2$ or —NH($C_1$-$C_4$)alkyl groups.

18. The method of claim 17, wherein X is selected from the group consisting of —$CH_2$—, —$CH_2$—$CH_2$—, —$CH_2$—$CH_2$—$CH_2$—, —$CH_2$—$CH_2$—$CH_2$—$CH_2$—, —$CH_2$—CH(OH)—, —CH(OH)—$CH_2$—, —CH(OH)—$CH_2$—$CH_2$—, —$CH_2$—CH(OH)—$CH_2$—, —$CH_2$—$CH_2$—CH(OH)— and —$CH_2$—CH(OH)—CH(OH)—$CH_2$—.

19. The method of claim 16, wherein X is selected from the group consisting of —CONR'—, —($C_1$-$C_4$)alkylCONR'—, —CONR'($C_1$-$C_4$)alkyl- and —($C_1$-$C_4$)alkylCONR'($C_1$-$C_4$)alkyl-, and wherein R' is H or ($C_1$-$C_3$)alkyl.

20. The method of claim 16, wherein Z is selected from the group consisting of —$CH_2$—, —$CH_2$—$CH_2$—, —$CH_2$—$CH_2$—$CH_2$—, —$CH_2$—$CH_2$—$CH_2$—$CH_2$—, —$CH_2$—CH(OH)—, —CH(OH)—$CH_2$—, —CH(OH)—$CH_2$—$CH_2$—, —CH($CH_2$OH)—$CH_2$—, —$CH_2$—CH(OH)—$CH_2$—, —$CH_2$—$CH_2$—CH(OH)— and —$CH_2$—CH(OH)—CH(OH)—$CH_2$—.

21. The method of claim 16, wherein A is $^{11}$C, $^{11}$C-Me or $^{18}$F.

22. The method of claim 16, wherein the compound is selected from the group consisting of:

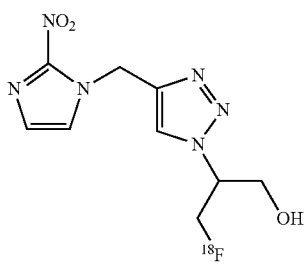

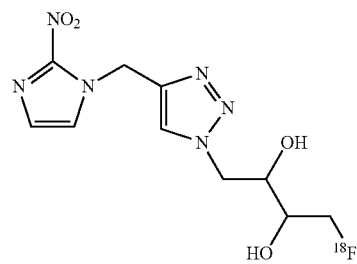

-continued

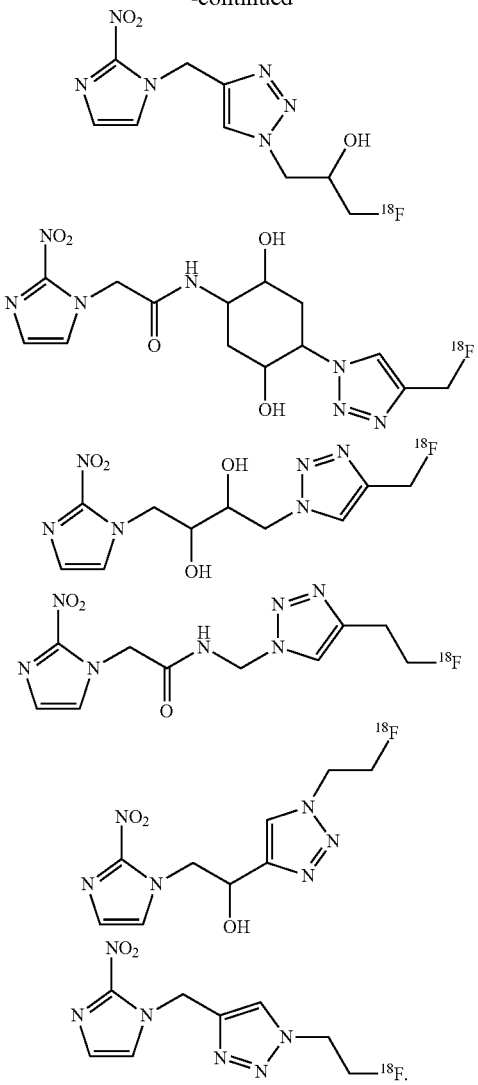

23. The method of claim 16 wherein the hypoxic cells are tumor cells or ischemic cells.

24. A method of preparing a compound of formula II or III, a mixture thereof or a pharmaceutically acceptable salt thereat optionally in the form of a single stereoisomer or mixtures of stereoisomers thereof:

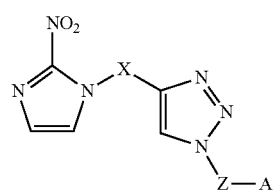

II

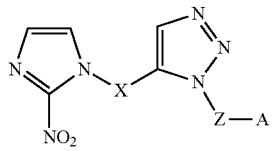

III wherein:

X is a $(C_1-C_{10})$alkylenyl, unsubstituted or substituted with 1, 2, 3 or 4 $X^1$, wherein at least one of the $(C_1-C_{10})$alkylenyl carbon atoms is optionally replaced by —CO—, —CONR'—, —NR'CO—, —NR'—, —O— and —S—, a $(C_3-C_8)$cycloalkyl or a $(C_3-C_8)$heterocycloalkyl ring, wherein at least one of the atoms of the $(C_3-C_8)$cycloalkyl or $(C_3-C_8)$heterocycloalkyl ring is unsubstituted or substituted with 1, 2, 3 or 4 $X^1$, or a combination thereof;

each $X^1$ is independently selected from the group consisting of hydroxyl, thiol, amino, alkyl, alkoxy, thioalkyl and halo;

Z is an $(C_1-C_{10})$alkylenyl group wherein at least one of the atoms of the $(C_1-C_{10})$alkylenyl group is optionally replaced by —CO—, —CONR"—, —NR"CO—, —NR"—, —O— and —S—, and wherein at least one of the atoms of the $(C_1-C_{10})$alkylenyl group is unsubstituted or substituted with 1, 2, 3 or 4 $X^1$;

A is a leaving group, $CH_3$, $CH_3O$, halo or a radioactive isotope; and

R' and R" are each independently H or are each independently selected from the group consisting of $(C_1-C_6)$alkyl, —CO$(C_1-C_3)$alkyl, —CONH$(C_1-C_3)$alkyl and —CO$_2(C_1-C_3)$alkyl;

the method comprising:

a) reacting an azide substituted compound A'-Z'-N$_3$ with an acetylene substituted nitroimidazole,

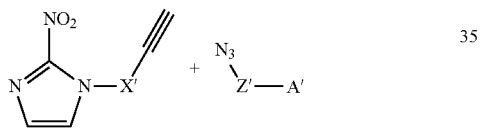

wherein:

X' is a $(C_1-C_{10})$alkylenyl, wherein at least one of the $(C_1-C_{10})$alkylenyl carbon atoms is optionally replaced by —CO—, —CONR'—, —NR'CO—, —NR'—, —O—, or —S—;

Z' is an $(C_1-C_{10})$alkylenyl group wherein at least one of the atoms of the $(C_1-C_{10})$alkylenyl group is optionally replaced by —CO—, —CONR"—, —NR"CO—, —NR"—, —O— and —S—, and wherein at least one of the atoms of the $(C_1-C_{10})$alkylenyl group is unsubstituted or substituted with 1, 2, 3 or 4 $X^{1'}$;

A' is a leaving group or a $(C_1-C_{10})$alkylenyl substituted or unsubstituted with a leaving group or a $(C_1-C_{10})$alkylenyl unsubstituted or substituted with 1, 2, 3 or 4 $X^{1'}$; and each $X^{1'}$ is independently selected from the group consisting of hydroxyl, thiol, amino, alkyl and alkoxy, thioalkyl and halo.

25. The method of claim 24 further comprising radiolabeling the product of step a) by the displacement of A' with a radiolabeling agent to form compound II or III or a mixture thereof, wherein A is either $^{18}F$ or $^{11}C$.

26. The method of claim 24, wherein a product of the reaction of the azide substituted compound A'-Z'-N$_3$ with an acetylene substituted nitroimidazole is a compound of formula II' or III', or a mixture thereof:

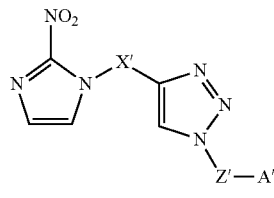

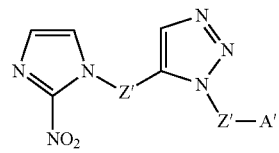

wherein A' does not comprise a leaving group, the method further comprising substituting A' with a leaving group to produce compound II'" or III'" or a mixture thereof:

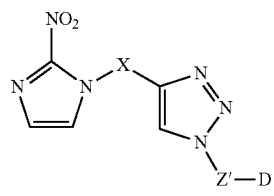

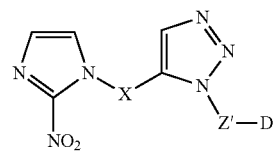

wherein D is a leaving group.

27. The method of claim 26, further comprising substituting the leaving group D with the radioactive isotope, A.

28. The method of claim 27, wherein the substituting step is comprised of reacting compound II" or III" or the mixture with $^{18}F$, K222 and MeCN.

29. A compound consisting of formula I:

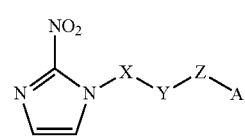

or a pharmaceutically acceptable salt thereof, optionally in the form of a single stereoisomer or mixtures of stereoisomers thereof, wherein:

X is a $(C_1-C_{10})$alkylenyl, wherein at least one of the $(C_1-C_{10})$alkylenyl carbon atoms is optionally replaced by —CO—, —CONR'—, —NR'CO—, —NR'—, —O—, —S—, a $(C_3-C_8)$cycloalkyl or a $(C_3-C_8)$heterocycloalkyl ring, wherein at least one of the atoms of the $(C_3-C_8)$cycloalkyl or a $(C_3-C_8)$heterocycloalkyl ring is unsubstituted or substituted with 1, 2, 3 or 4 $X^1$, or a combination thereof;

each $X^1$ is independently selected from the group consisting of hydroxyl, thiol, amino, alkyl, alkoxy, thioalkyl and halo;

Y is a triazolyl of the formula:

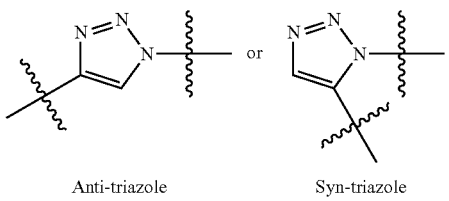

Anti-triazole    Syn-triazole

Z is an $(C_1-C_{10})$alkylenyl group wherein at least one of the atoms of the $(C_1-C_{10})$alkylenyl group is optionally replaced by —CO—, —CONR"—, —NR"CO—, —NR"—, —O— and —S—, and wherein at least one of the atoms of the $(C_1-C_{10})$alkylenyl group is unsubstituted or substituted with 1, 2, 3 or 4 $X^1$;

A is a leaving group, $CH_3$, $CH_3O$, halo or a radioactive isotope; and

R' and R" are each independently H or are each independently selected from the group consisting of $(C_1-C_6)$ alkyl, —CO$(C_1-C_3)$alkyl, —CONH$(C_1-C_3)$alkyl and —CO$_2$$(C_1-C_3)$alkyl.

30. The compound of claim 29, wherein at least one carbon atom of Z is substituted with AcO.

31. A compound consisting of the formula I:

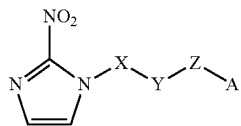

I wherein:

X is a $(C_1-C_{10})$alkylenyl, unsubstituted or substituted with 1, 2, 3 or 4 $X^1$;

each $X^1$ is independently selected from the group consisting of hydroxyl, thiol, amino, alkyl, alkoxy, thioalkyl and halo;

Y is a triazolyl of the formula:

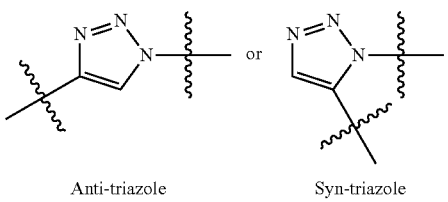

Anti-triazole    Syn-triazole

Z is an $(C_1-C_{10})$alkylenyl group wherein one of the carbon atoms of the $(C_1-C_{10})$alkylenyl group is optionally replaced by a group selected from —CO—, —CONR"—, —NR"CO—, —NR"—, —O— and —S—, and wherein the $(C_1-C_{10})$alkylenyl group is unsubstituted or substituted with 1, 2, 3 or 4 $X^1$;

A is a leaving group, $CH_3$, $CH_3O$, halo or a radioactive isotope; and

R" is H or is selected from the group consisting of $(C_1-C_6)$ alkyl, —CO$(C_1-C_3)$alkyl, —CONH$(C_1-C_3)$alkyl and —CO$_2$$(C_1-C_3)$alkyl.

* * * * *